United States Patent
Roe et al.

(10) Patent No.: US 8,491,558 B2
(45) Date of Patent: Jul. 23, 2013

(54) ABSORBENT ARTICLE WITH IMPREGNATED SENSATION MATERIAL FOR TOILET TRAINING

(75) Inventors: Donald Carroll Roe, West Chester, OH (US); Jennifer Joan Nandrea, Cincinnati, OH (US); Masaharu Nishikawa, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/724,922

(22) Filed: Mar. 16, 2007

(65) Prior Publication Data
US 2007/0233028 A1    Oct. 4, 2007

Related U.S. Application Data

(60) Provisional application No. 60/788,489, filed on Mar. 31, 2006.

(51) Int. Cl.
| A61F 13/15 | (2006.01) |
| A61F 13/45 | (2006.01) |
| A61F 13/51 | (2006.01) |
| A61F 13/511 | (2006.01) |

(52) U.S. Cl.
USPC ............. 604/385.3; 604/385.24; 604/385.25; 604/385.26; 604/385.27; 604/385.28; 604/385.29

(58) Field of Classification Search
USPC ............... 604/358, 361, 378, 385.23, 385.24, 604/385.25, 385.26, 385.27
See application file for complete search history.

(56) References Cited

U.S. PATENT DOCUMENTS

| 3,848,594 A | 11/1974 | Buell |
| 3,860,003 A | 1/1975 | Buell |
| 3,881,491 A | 5/1975 | Whyte |
| 3,911,173 A | 10/1975 | Sprague, Jr. |
| 3,921,232 A | 11/1975 | Whyte |
| 3,929,135 A | 12/1975 | Thompson |
| 4,020,153 A | 4/1977 | Rowsell et al. |

(Continued)

FOREIGN PATENT DOCUMENTS

| EP | 454105 B1 | 11/1995 |
| EP | 547497 | 6/1997 |

(Continued)

OTHER PUBLICATIONS

U.S. Appl. No. 11/351,745, filed Feb. 10, 2006, Roe et al.

(Continued)

*Primary Examiner* — Adam Marcetich
(74) *Attorney, Agent, or Firm* — Abbey A. Lopez; Amy M. Foust; Charles R. Ware

(57) ABSTRACT

An absorbent article includes a backsheet having a longitudinal axis, a topsheet attached to the backsheet and having a body-facing surface, and an absorbent core disposed between the backsheet and the topsheet. The article may also include barrier leg cuffs. The article further includes a sensation member, which sensation member may be defined in part by the topsheet or may be separate from the topsheet. The sensation member may be a wetness sensation member, a temperature sensation member, a tactile agent, or a combination thereof. Visible and/or tactile indicia may be associated with the sensation member.

16 Claims, 9 Drawing Sheets

U.S. PATENT DOCUMENTS

| | | | |
|---|---|---|---|
| 4,022,210 A | 5/1977 | Glassman | |
| 4,032,661 A | 6/1977 | Rowsell et al. | |
| 4,033,994 A | 7/1977 | Watson et al. | |
| 4,034,109 A | 7/1977 | Rowsell et al. | |
| 4,070,449 A | 1/1978 | Rowsell et al. | |
| 4,070,496 A | 1/1978 | Rowsell et al. | |
| 4,089,765 A | 5/1978 | Dudley | |
| 4,150,052 A | 4/1979 | Watson et al. | |
| 4,153,679 A | 5/1979 | Rowsell et al. | |
| 4,178,459 A | 12/1979 | Watson et al. | |
| 4,193,936 A | 3/1980 | Watson et al. | |
| 4,226,988 A | 10/1980 | Watson et al. | |
| 4,289,794 A | 9/1981 | Kleiner et al. | |
| 4,296,093 A | 10/1981 | Rowsell et al. | |
| 4,296,255 A | 10/1981 | Roswell et al. | |
| 4,324,246 A | 4/1982 | Mullane et al. | |
| 4,342,314 A | 8/1982 | Radel et al. | |
| 4,459,425 A | 7/1984 | Amano et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |
| 4,816,025 A | 3/1989 | Foreman | |
| 4,834,735 A | 5/1989 | Alemany et al. | |
| 4,842,666 A | 6/1989 | Werenicz | |
| 4,846,815 A | 7/1989 | Scripps | |
| 4,888,231 A | 12/1989 | Angstadt | |
| 4,892,536 A | 1/1990 | Desmarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,968,312 A | 11/1990 | Khan | |
| 4,981,747 A | 1/1991 | Morman | |
| 4,990,147 A | 2/1991 | Freeland | |
| 5,006,394 A | 4/1991 | Baird | |
| 5,026,364 A | 6/1991 | Robertson | |
| 5,037,416 A | 8/1991 | Allen et al. | |
| 5,062,840 A | 11/1991 | Holt et al. | |
| 5,092,861 A | 3/1992 | Nomura et al. | |
| 5,116,662 A | 5/1992 | Morman | |
| 5,124,188 A | 6/1992 | Roe et al. | |
| 5,137,537 A | 8/1992 | Herron et al. | |
| 5,147,345 A | 9/1992 | Young et al. | |
| 5,151,092 A | 9/1992 | Buell et al. | |
| 5,156,793 A | 10/1992 | Buell et al. | |
| 5,167,653 A * | 12/1992 | Igaue et al. | 604/385.04 |
| 5,167,655 A * | 12/1992 | McCoy | 604/396 |
| 5,167,897 A | 12/1992 | Weber et al. | |
| 5,171,236 A | 12/1992 | Dreier et al. | |
| 5,178,139 A * | 1/1993 | Angelillo et al. | 607/114 |
| 5,221,274 A | 6/1993 | Buell et al. | |
| 5,226,992 A | 7/1993 | Morman | |
| 5,246,432 A * | 9/1993 | Suzuki et al. | 604/385.25 |
| 5,246,433 A | 9/1993 | Hasse et al. | |
| 5,260,345 A | 11/1993 | Desmarais et al. | |
| 5,266,592 A | 11/1993 | Grub et al. | |
| 5,269,775 A | 12/1993 | Freeland et al. | |
| 5,306,266 A | 4/1994 | Freeland | |
| 5,318,555 A | 6/1994 | Siebers et al. | |
| 5,330,459 A | 7/1994 | Lavon et al. | |
| 5,336,545 A | 8/1994 | Morman | |
| 5,342,338 A | 8/1994 | Roe | |
| 5,342,343 A | 8/1994 | Kitaoka et al. | |
| 5,348,750 A | 9/1994 | Greenberg | |
| 5,380,313 A | 1/1995 | Goulait et al. | |
| 5,387,207 A | 2/1995 | Dyer et al. | |
| 5,397,316 A | 3/1995 | Lavon et al. | |
| 5,397,318 A | 3/1995 | Dreier | |
| 5,407,439 A | 4/1995 | Goulait | |
| 5,425,726 A | 6/1995 | Shimizu et al. | |
| 5,428,076 A | 6/1995 | Roe | |
| 5,460,622 A | 10/1995 | Dragoo et al. | |
| 5,514,121 A | 5/1996 | Roe et al. | |
| 5,518,801 A | 5/1996 | Chappell et al. | |
| 5,540,671 A | 7/1996 | Dreier | |
| 5,540,673 A | 7/1996 | Thomas et al. | |
| 5,542,942 A | 8/1996 | Kline et al. | |
| 5,554,142 A | 9/1996 | Dreier et al. | |
| 5,554,143 A | 9/1996 | Roe et al. | |
| 5,554,145 A | 9/1996 | Roe et al. | |
| 5,567,609 A | 10/1996 | Sarras, Jr. et al. | |
| 5,569,233 A | 10/1996 | Goulait | |
| 5,569,234 A | 10/1996 | Buell et al. | |
| 5,571,096 A | 11/1996 | Dobrin et al. | |
| 5,580,411 A | 12/1996 | Nease et al. | |
| 5,599,338 A * | 2/1997 | Enloe | 604/385.28 |
| 5,607,760 A | 3/1997 | Roe | |
| 5,608,119 A | 3/1997 | Amano et al. | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,649,914 A | 7/1997 | Glaug et al. | |
| 5,653,703 A | 8/1997 | Roe et al. | |
| 5,658,268 A | 8/1997 | Johns et al. | |
| 5,662,637 A * | 9/1997 | Kitaoka et al. | 604/385.28 |
| 5,669,900 A | 9/1997 | Bullwinkel et al. | |
| 5,681,298 A | 10/1997 | Brunner et al. | |
| 5,681,303 A * | 10/1997 | Mills et al. | 604/385.26 |
| 5,702,376 A | 12/1997 | Glaug et al. | |
| H1732 H | 6/1998 | Johnson | |
| 5,797,892 A | 8/1998 | Glaug et al. | |
| 5,851,204 A * | 12/1998 | Mizutani | 604/385.04 |
| 5,865,823 A | 2/1999 | Curro | |
| 5,865,824 A * | 2/1999 | Chen et al. | 604/378 |
| 5,883,028 A | 3/1999 | Morman et al. | |
| 5,885,264 A | 3/1999 | Matsushita | |
| 5,891,124 A | 4/1999 | Nomura et al. | |
| 5,897,545 A | 4/1999 | Kline et al. | |
| 5,938,648 A | 8/1999 | Lavon et al. | |
| 5,941,864 A | 8/1999 | Roe | |
| 5,947,947 A | 9/1999 | Tanzer et al. | |
| 5,957,908 A | 9/1999 | Kline et al. | |
| 5,968,025 A | 10/1999 | Roe et al. | |
| 5,977,430 A | 11/1999 | Roe et al. | |
| 5,989,380 A | 11/1999 | Frischer | |
| 5,997,520 A | 12/1999 | Ahr et al. | |
| 6,004,306 A | 12/1999 | Robles et al. | |
| 6,010,490 A | 1/2000 | Freeland et al. | |
| 6,013,063 A | 1/2000 | Roe et al. | |
| 6,107,535 A | 8/2000 | Rossini et al. | |
| 6,107,537 A | 8/2000 | Elder et al. | |
| 6,114,597 A | 9/2000 | Romare | |
| 6,118,041 A | 9/2000 | Roe et al. | |
| 6,120,487 A | 9/2000 | Ashton | |
| 6,120,488 A | 9/2000 | Vanrijswijck et al. | |
| 6,120,489 A | 9/2000 | Johnson et al. | |
| 6,120,783 A | 9/2000 | Roe et al. | |
| 6,123,694 A * | 9/2000 | Pieniak et al. | 604/385.28 |
| 6,146,367 A * | 11/2000 | Otsubo et al. | 604/385.01 |
| 6,153,209 A | 11/2000 | Vega et al. | |
| 6,156,024 A | 12/2000 | Schulte et al. | |
| 6,156,424 A | 12/2000 | Taylor | |
| 6,166,285 A | 12/2000 | Schulte et al. | |
| 6,168,584 B1 | 1/2001 | Allen et al. | |
| 6,169,225 B1 | 1/2001 | Otsubo | |
| 6,186,991 B1 | 2/2001 | Roe et al. | |
| 6,214,788 B1 | 4/2001 | Velazco et al. | |
| 6,229,063 B1 | 5/2001 | Shimoe et al. | |
| 6,253,159 B1 | 6/2001 | Bett et al. | |
| 6,264,641 B1 | 7/2001 | Van Gompel et al. | |
| 6,266,436 B1 | 7/2001 | Bett et al. | |
| 6,267,974 B1 | 7/2001 | Suares et al. | |
| 6,280,428 B1* | 8/2001 | Lash et al. | 604/385.04 |
| 6,297,424 B1 | 10/2001 | Olson et al. | |

| | | |
|---|---|---|
| 6,297,434 B1 | 10/2001 | Martello |
| 6,307,119 B1 | 10/2001 | Cammarota et al. |
| 6,313,372 B1 | 11/2001 | Suzuki |
| 6,320,096 B1 | 11/2001 | Inoue et al. |
| 6,328,982 B1 | 12/2001 | Shiroyama et al. |
| 6,359,168 B1 | 3/2002 | Frerot et al. |
| 6,428,526 B1 | 8/2002 | Heindel et al. |
| 6,432,098 B1 | 8/2002 | Kline et al. |
| 6,443,940 B1 | 9/2002 | Ashton et al. |
| 6,444,064 B1 | 9/2002 | Henry et al. |
| 6,448,467 B1 | 9/2002 | Herrlein et al. |
| 6,465,073 B1 | 10/2002 | Morman et al. |
| 6,479,154 B1 | 11/2002 | Walton et al. |
| 6,482,191 B1 | 11/2002 | Roe et al. |
| 6,503,236 B1 | 1/2003 | Uitenbroek et al. |
| 6,548,431 B1 | 4/2003 | Bansal et al. |
| 6,576,810 B1* | 6/2003 | Underhill et al. ............ 604/361 |
| 6,579,274 B1 | 6/2003 | Morman et al. |
| 6,583,722 B2* | 6/2003 | Jeutter et al. ............ 340/573.1 |
| 6,590,136 B1 | 7/2003 | Young et al. |
| 6,592,884 B2 | 7/2003 | Hofmann et al. |
| 6,617,016 B2 | 9/2003 | Zhang et al. |
| 6,623,465 B1 | 9/2003 | Roe et al. |
| 6,623,837 B2 | 9/2003 | Morman et al. |
| 6,627,564 B1 | 9/2003 | Morman et al. |
| 6,627,786 B2 | 9/2003 | Roe et al. |
| 6,635,797 B2 | 10/2003 | Olson et al. |
| 6,642,427 B2 | 11/2003 | Roe et al. |
| 6,657,100 B1* | 12/2003 | Underhill et al. ............ 604/361 |
| 6,676,646 B2 | 1/2004 | Bast et al. |
| 6,680,265 B1 | 1/2004 | Smith et al. |
| 6,680,422 B2 | 1/2004 | Roe |
| 6,692,475 B2 | 2/2004 | Mishima |
| 6,702,795 B2 | 3/2004 | Klemp |
| 6,716,441 B1 | 4/2004 | Osborne et al. |
| 6,726,668 B2 | 4/2004 | Underhill et al. |
| 6,727,404 B2 | 4/2004 | Ruman et al. |
| 6,743,314 B2 | 6/2004 | Henry et al. |
| 6,766,817 B2 | 7/2004 | Da Silva |
| 6,770,064 B1* | 8/2004 | Ruscher ............ 604/385.01 |
| 6,811,865 B2 | 11/2004 | Morman et al. |
| 6,849,324 B2 | 2/2005 | Meece et al. |
| 6,875,710 B2 | 4/2005 | Eaton et al. |
| 6,881,206 B2 | 4/2005 | Underhill et al. |
| 6,884,906 B2 | 4/2005 | Dewis et al. |
| 6,905,488 B2 | 6/2005 | Olson |
| 6,909,028 B1 | 6/2005 | Shawver et al. |
| 6,918,404 B2 | 7/2005 | Dias da Silva |
| 6,929,819 B2 | 8/2005 | Underhill et al. |
| 6,943,894 B2 | 9/2005 | Kitahara |
| 6,955,667 B1* | 10/2005 | Tanaka et al. ............ 604/385.24 |
| 6,955,733 B2 | 10/2005 | Miller et al. |
| 6,957,160 B2 | 10/2005 | Miller et al. |
| 6,958,432 B2 | 10/2005 | Underhill et al. |
| 6,960,834 B2 | 11/2005 | Nakamura et al. |
| 7,002,055 B2 | 2/2006 | Long et al. |
| 7,033,341 B2 | 4/2006 | Mishima |
| 7,056,411 B2 | 6/2006 | Desai et al. |
| 7,066,586 B2 | 6/2006 | Da Silva |
| 7,123,981 B2 | 10/2006 | Dollevoet et al. |
| 7,169,137 B2 | 1/2007 | Shimada |
| 7,195,729 B2 | 3/2007 | Jackson et al. |
| 7,223,818 B2 | 5/2007 | Autran et al. |
| 7,285,255 B2 | 10/2007 | Kadlec et al. |
| 7,301,036 B2 | 11/2007 | Parmee et al. |
| 2001/0021836 A1* | 9/2001 | Kashiwagi ............ 604/385.24 |
| 2002/0062117 A1 | 5/2002 | Raufman et al. |
| 2002/0111596 A1 | 8/2002 | Fletcher et al. |
| 2002/0128625 A1* | 9/2002 | Tanaka et al. ............ 604/385.28 |
| 2002/0138062 A1 | 9/2002 | Kuen et al. |
| 2003/0060794 A1 | 3/2003 | Olson |
| 2003/0065298 A1 | 4/2003 | Krishnaswamy Mirle et al. |
| 2003/0077430 A1 | 4/2003 | Grimm et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0114807 A1 | 6/2003 | Underhill et al. |
| 2003/0114821 A1 | 6/2003 | Underhill et al. |
| 2003/0120240 A1 | 6/2003 | Buell et al. |
| 2003/0125682 A1 | 7/2003 | Olson et al. |
| 2003/0125689 A1 | 7/2003 | Olson et al. |
| 2003/0145937 A1* | 8/2003 | Underhill et al. ............ 156/146 |
| 2003/0162458 A1 | 8/2003 | Tsujiyama et al. |
| 2003/0199845 A1* | 10/2003 | Roe et al. ............ 604/385.101 |
| 2004/0067970 A1 | 4/2004 | Foster et al. |
| 2004/0071780 A1 | 4/2004 | Lillard et al. |
| 2004/0081680 A1 | 4/2004 | Pesce et al. |
| 2004/0082654 A1 | 4/2004 | Pesce et al. |
| 2004/0092902 A1 | 5/2004 | Hoffman et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0162536 A1 | 8/2004 | Becker et al. |
| 2004/0167486 A1 | 8/2004 | Busam et al. |
| 2004/0191279 A1 | 9/2004 | Klofta |
| 2004/0193133 A1 | 9/2004 | Desai et al. |
| 2004/0211696 A1 | 10/2004 | Underhill et al. |
| 2004/0220540 A1 | 11/2004 | Underhill et al. |
| 2004/0254549 A1 | 12/2004 | Olson et al. |
| 2004/0254550 A1 | 12/2004 | Huang et al. |
| 2005/0027274 A1 | 2/2005 | Suzuki et al. |
| 2005/0049553 A1 | 3/2005 | Triplett et al. |
| 2005/0049568 A1 | 3/2005 | Underhill et al. |
| 2005/0096612 A1 | 5/2005 | Davis et al. |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |
| 2005/0139713 A1 | 6/2005 | Weber et al. |
| 2005/0147785 A1 | 7/2005 | Ahn et al. |
| 2005/0177123 A1 | 8/2005 | Catalan |
| 2005/0214461 A1 | 9/2005 | Desai et al. |
| 2005/0222546 A1 | 10/2005 | Vargo et al. |
| 2006/0025737 A1 | 2/2006 | Song et al. |
| 2006/0212010 A1 | 9/2006 | Roe et al. |
| 2006/0212018 A1 | 9/2006 | Roe et al. |
| 2006/0224132 A1 | 10/2006 | Roe et al. |
| 2006/0247594 A1 | 11/2006 | Nickel et al. |
| 2007/0032766 A1 | 2/2007 | Liu et al. |
| 2007/0049884 A1 | 3/2007 | Long et al. |
| 2007/0073261 A1 | 3/2007 | Ashton et al. |
| 2007/0287982 A1 | 12/2007 | Lodge et al. |
| 2007/0287983 A1 | 12/2007 | Lodge et al. |

FOREIGN PATENT DOCUMENTS

| | | |
|---|---|---|
| EP | 0 937 446 A2 | 8/1999 |
| EP | 1 287 799 A2 | 3/2003 |
| WO | WO-94/14395 A1 | 7/1994 |
| WO | WO-95/16746 | 6/1995 |
| WO | WO-95 16746 A1 | 6/1995 |
| WO | WO-02/091968 A2 | 11/2002 |
| WO | WO-2004/071780 A2 | 8/2004 |
| WO | WO-2005/041834 A1 | 5/2005 |
| WO | WO-2005/102239 A1 | 11/2005 |
| WO | WO-2006 017518 A2 | 2/2006 |

OTHER PUBLICATIONS

U.S. Appl. No. 11/724,713, filed Mar. 16, 2007, Roe et al.
U.S. Appl. No. 11/724,709, filed Mar. 16, 2007, Roe et al.
U.S. Appl. No. 11/724,851, filed Mar. 16, 2007, Roe et al.
U.S. Appl. No. 11/724,838, filed Mar. 16, 2007, Roe et al.
U.S. Appl. No. 11/599,829, filed Jun. 9, 2007, Autran et al.
PCT Search Report mailed Aug. 23, 2006 (4 pages).
"Pampers Ultra Trainers" package, Size 3 from Finneytown Kroger's dated Oct. 3, 1998. 2 pages.
Timothy R. Scrum, MD, et al. —Sequential Acquisition of Toilet-Training Skills: A Descriptive Study of Gender and Age Differences in Normal Children, *Pediatrics*, Mar. 2002, 7 pages vol. 109, No. 3.

* cited by examiner

ABSORBENT ARTICLE WITH IMPREGNATED SENSATION MATERIAL FOR TOILET TRAINING

CROSS-REFERENCE TO RELATED APPLICATIONS

This application claims the benefit of U.S. Provisional Application No. 60/788,489 filed on Mar. 31, 2006, the substance of which is incorporated herein by reference.

The present disclosure generally relates to absorbent articles, including diapers, training pants, pull-on diapers, absorbent inserts, diaper holders and liners, and the like, and in particular to an absorbent article with a sensation material impregnated in a body-facing component, which may be adapted for use in urinary toilet training.

BACKGROUND OF THE INVENTION

Absorbent articles are well known in the art. These articles typically have an absorbent assembly held or positioned in proximity to the body of a wearer during use in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. Disposable diapers typically comprise a single design available in different sizes to fit a variety of wearers ranging from newborns to toddlers undergoing toilet training. The design of the diaper typically affects performance, such as the ability to absorb and contain bodily waste. The fit of the diaper on the wearer's body is typically affected by, for example, the size of the diaper waist opening, the size of the openings around the thighs, and the length or "pitch" of the diaper.

The toilet training stage may be referred to as the "point of exit" from the diaper product category because toddlers who have successfully completed toilet training typically no longer wear diapers. The age at which children are toilet trained in "developed" countries has increased steadily over the past several decades and is now in the range of about 24-48 months. One reason for which toilet training has become delayed is that significant technical improvements have been made in diaper dryness and comfort. For example, when wearing a typical modern diaper, the child may have dry skin even after one or more occurrences of urination. As a result, the child may feel little or no discomfort and often may not even be aware that he or she has urinated.

Some parents may have the child wear cotton training patent or cotton underwear during urinary training so the child feels discomfort following urination in his or her "pants." It is believed that such discomfort assists with learning or provides motivation to learn to voluntarily retain urine (at least until the child can urinate is a socially acceptable time/location). Cloth training pants leave the skin wet and, due to their high breathability, promote evaporative cooling of the skin, further enhancing discomfort. The current tradeoff in this approach, however, is that cloth training pants have poor urine containment, often leading to wet clothing and wet surroundings, e.g., carpeting, furniture, etc. Clearly, there is a need to provide a training signal to the child undergoing urinary toilet training while preventing urine leakage and unnecessary changes of clothing. Numerous attempts have been made in the art to provide a suitable diaper or training pant for toilet training. However, such attempts typically have the shortcoming of requiring a complex and expensive design while also being difficult to manufacture. Further, previous attempts have required numerous additional components to deliver the benefit.

Thus, it would be desirable to provide an article that can facilitate urinary toilet training by enhancing a wearer's awareness that urination has occurred while at the same time providing the protection of an absorbent article to prevent soiling of the wearer's clothing and surroundings. Particularly, it would be desirable to provide such an article in a form that is relatively inexpensive and easy to manufacture while also providing an effective signal of urination by ensuring that the wearer feels an uncomfortable sensation resulting from urination.

SUMMARY OF THE INVENTION

In accordance with one aspect of the present invention, an absorbent article includes a backsheet having a longitudinal axis, a topsheet attached to the backsheet and having a body-facing surface and first and second sides, and an absorbent core disposed between the backsheet and the topsheet. First and second spaced barrier leg cuffs are attached to the topsheet parallel to the longitudinal axis. The topsheet first side is attached to the first barrier leg cuff and the topsheet second side is attached to the second barrier leg cuff such that said body-facing surface of said topsheet is spaced a distance upwardly from said absorbent core. A sensation member is provided that includes the topsheet at least partially impregnated with a sensation agent.

In accordance with another aspect of the present invention, an absorbent article includes a backsheet having a longitudinal axis, a topsheet attached to the backsheet and having a body-facing surface and an opposite surface facing the backsheet, and an absorbent core disposed between the backsheet and the topsheet. The absorbent article further includes a sensation member including a sensation agent at least partially impregnated in a region of the topsheet on one of the body-facing surface and the opposite surface. The region of the topsheet is spaced a distance upwardly from said absorbent core.

In accordance with still another aspect of the present invention, an absorbent article includes a backsheet, a topsheet attached to the backsheet and having a body-facing surface and an opposite surface facing the backsheet, and an absorbent core disposed between the backsheet and the topsheet. The absorbent article further includes a sensation member overlaying a portion of the body-facing surface of the topsheet. The sensation member has a sensation agent at least partially impregnated therein. The sensation member is spaced upwardly from the topsheet.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 3B is a cross-sectional view of the article shown in FIG. 3a;

FIG. 5B is a cross-sectional view of the article shown in FIG. 5a;

FIG. 6B is a cross-sectional view of the article shown in FIG. 6a.

DETAILED DESCRIPTION OF THE INVENTION

Definitions

Figure 1:
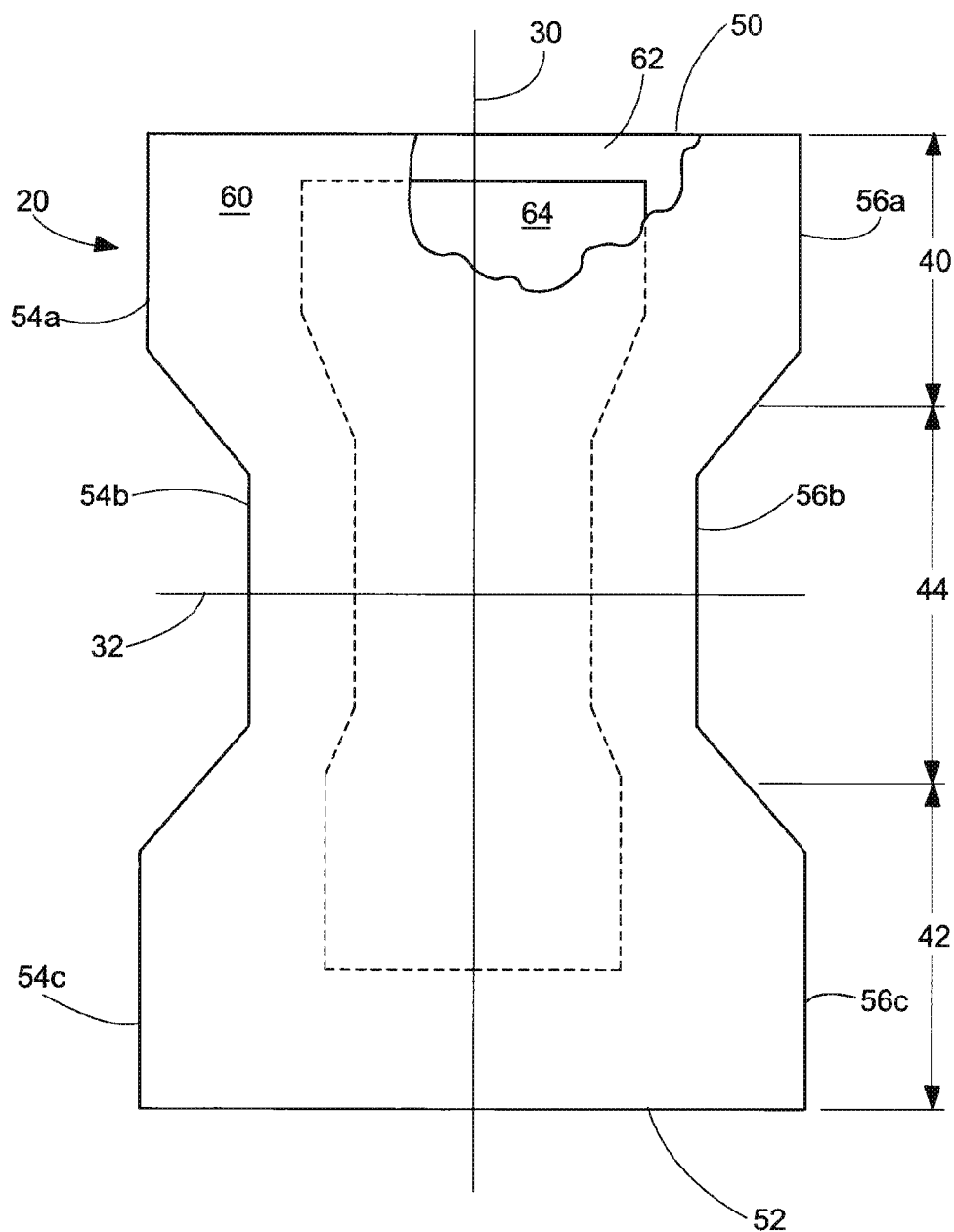
FIG. 1 is a plan view of an absorbent article with a section of a topsheet removed to expose an underlying absorbent core.

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "associated with", in relation to highlighting, refers at least to highlighting that is on an element or to highlighting that is disposed proximate to an element.

The term "associative correlation" refers to establishing a mutual or reciprocal relation between the visible highlighting and that with which it is being associatively correlated so that an association, i.e. a mental connection or bond, is formed between the two. This term is used in the context of associatively correlating the respective visible forms of the visible highlighting and an externally visible graphics in or on the absorbent article as well as in the context of associatively correlating the visible highlighting or graphics with the concept of urinary toilet training. For example, associatively correlated graphics may serve in concert to draw attention to an opportunity for urinary toilet training when an absorbent article is viewed prior to its being worn, to provide an externally visible reminder of the presence of the sensation material in the absorbent article while it is being worn, etc. Similarly, visible highlighting that provides a visual reference to a topic related to urinary toilet training, such as dryness, wetness, or protection from wetness, may serve to associatively correlate the visible highlighting to the concept of urinary toilet training and thereby facilitate an opportunity for urinary toilet training.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "caregiver" refers to a person other than the child, such as, a parent, babysitter, family member, teacher, day care worker, or other person who is able to provide sufficient assistance to the child to complete a personal hygiene task.

The term "character image" refers to a graphic containing an anthropomorphic image, and in particular an image having or suggesting human form or appearance which ascribes human motivations, characteristics or behavior to inanimate objects, animals, natural phenomena, toys, cartoon characters, or the like. The character image may be associated with popular characters in the media, advertising or well known in a particular culture. Ideally they are characters that the user, particularly if a child, cares about and wants to identify with.

The term "coloration" refers to the arrangement or degree of coloring especially when used to visibly differentiate an object or a portion of an object in order to visibly highlight it.

The term "coloring" refers to the effect produced by applying or combining colors in and/or on an object or a portion of an object.

The term "diaper" refers to an absorbent article generally worn by infants and incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The term "graphic" refers to a product of graphic art or a graphic representation in a pictorial form. A graphic may be a symbol, shape, image, text, or other form of indicia.

The terms "interactively interrelated", "interactively unrelated", "related in subject matter", "unrelated in subject matter", and "related by a common story line" are intended to have the same meanings as in U.S. Pat. Nos. 6,297,424, 6,635,797, and 6,307,119.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

The term "lateral" or "transverse" refers to a direction running at a 90 degree angle to the longitudinal direction and includes directions within ±45° of the lateral direction.

The term "longitudinal" refers to a direction running parallel to the maximum linear dimension of the article and includes directions within ±45° of the longitudinal direction.

The terms "pre-literate" and "incapable of reading" are used interchangeably herein to mean the inability of a child to correctly understand, comprehend and follow prompts written in a language that the child can speak without assistance of a caregiver. The ability of a child to recognize letters and/or read one or two isolated words still means that the child is "incapable of reading" since he or she is unable to understand, comprehend and follow such written prompts, without assistance. However, this definition of "incapable of reading" does not exclude the child from being able to understand, comprehend and follow visual prompts which are presented in the form of drawings, icons, symbols, gestures, cartoons and the like.

The term "refastenable" refers to the property of two elements being capable of releasable attachment, separation, and subsequent releasable reattachment without substantial permanent deformation or rupture.

The terms "releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

The term "solid coloring" refers to the unbroken, i.e., uninterrupted, coloring of an area as contrasted with the discrete line-like form of some graphics.

The term "toilet training" refers to the development of continence, which is the ability to voluntarily retain one's urine and feces. Individuals who are incontinent are unable to voluntarily retain their bodily discharges and, instead, urinate and defecate reflexively. For example, newborn babies are incontinent. Coincident with the development of continence, children typically develop the ability to voluntarily urinate and defecate, and cease reflexive elimination. This development of continence and of voluntary elimination, in place of reflexive elimination, may be accelerated and/or guided by caregivers through associative and conditioning techniques of training the child. For the purpose of the present disclosure, the term "toilet training" is used to denote training both for continence, itself, and for the voluntary elimination that is associated with continence. It is also noted that the term "toilet training" is synonymous with the term "potty training".

The term "training pants" refers to an absorbent article generally worn by infants and incontinent persons about the lower torso and having the general form of a pair of short pants that can be applied or removed from the wearer without unfastening.

The term "unitary" refers to an absorbent article that is formed of separate parts united together to form a coordinated entity so as to not require separate manipulative parts like a separate holder and liner.

The term "visible" refers to the quality of being capable of being seen by the naked eye under conditions of normal room lighting or in natural light during the daytime. Becoming "more visible" or "less visible" means changing in visibility to a noticeable extent when viewed under a generally constant or equal lighting condition.

The term "visible highlighting" refers to the visible differentiation of an object such that it noticeably stands out from its surroundings, e.g., by differing in coloration, hue, or tint, by differing in lightness, darkness, or contrast, by differing due to the presence or absence of graphical or solid color forms, or by any other variation serving to create noticeable visible differentiation.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The term "x-y plane" refers to the generally planar structure of a sheet material defined by its length and width and lies between the sheet material's two major surfaces regardless of whether or not the sheet material is flat or curved.

The term "z-direction" refers to the direction through the thickness of a sheet material and generally orthogonal to the x-y plane.

The term "wetness sensation member" or "sensation member" refers to a structure that applies a signal to the skin of the wearer in response to an insult of urine. The sensation member can include one or more wetness sensation agents which, in turn, can comprise one or more sensation materials.

The term "sensation member" is analogous to "sensory element member" and "wetness sensation member" and "feedback response member" as used herein or in co-pending application Ser. Nos. 60/788,482, 60/788,505, 60/788,343, 60/788,489 and 60/788,415 all filed on Mar. 31, 2006.

The term "wetness sensation agent" or "sensation agent" refers to one or more materials intended to produce a predetermined response (e.g., temperature sensation, wetness sensation, tactile sensation) in response to an insult of urine.

The term "wetness sensation material" or "sensation material" refers to the one or more materials that make up a given sensation agent.

FIG. 1 is a plan view of an exemplary disposable absorbent article 20 in its flat, uncontracted state, i.e., without elastic-induced contraction. Portions of the article 20 have been cut away to more clearly show the underlying structure of the disposable absorbent article 20. As illustrated, the portion of the disposable absorbent article 20 that contacts the wearer faces the viewer (i.e., showing the interior or inner side of the article). The disposable absorbent article 20 has a longitudinal axis 30 and a transverse axis 32.

One end portion of the disposable absorbent article 20 is configured as a first waist region 40 of the disposable absorbent article 20. The opposite end portion is configured as a second waist region 42 of the disposable absorbent article 20. The waist regions 40 and 42 generally comprise those portions of the disposable absorbent article 20 which, when worn, encircle the waist of the wearer. The waist regions 40 and 42 may include elastic elements such that they gather about the waist of the wearer to provide improved fit and containment. An intermediate portion of the disposable absorbent article 20 is configured as a crotch region 44, which extends longitudinally between the first and second waist regions 40 and 42. The crotch region 44 is that portion of the disposable absorbent article 20 which, when the disposable absorbent article 20 is worn, is generally positioned between the legs of the wearer.

The disposable absorbent article 20 has a laterally extending first waist edge 50 in the first waist region 40 and a longitudinally opposing and laterally extending second waist edge 52 in the second waist region 42. The disposable absorbent article 20 has a first side edge 54 and a laterally opposing second side edge 56, both side edges extending longitudinally between the first waist edge 50 and the second waist edge 52. The portion of the first side edge 54 in the first waist region 40 is designated 54a, the portion in the crotch region 44 is designated 54b, and the portion in the second waist region 42 is designated 54c. The corresponding portions of the second side edge 56 are designated 56a, 56b, and 56c, respectively.

The disposable absorbent article 20 preferably comprises a water-permeable topsheet 60, a water-impermeable backsheet 62, and an absorbent assembly or core 64, which may be disposed between the topsheet 60 and the backsheet 62 with the topsheet 60 attached to the backsheet 62. The topsheet 60 may be fully or partially elasticized or may be foreshortened so as to provide a void space between the topsheet 60 and the core 64. As explained below, a fully or partially elasticized topsheet 60 may also to tend to draw a sensation member 80, which can include the topsheet 60 in some embodiments, against the skin of the wearer. Exemplary structures including elasticized or foreshortened topsheets are described in greater detail in U.S. Pat. Nos. 4,892,536; 4,990,147; 5,037,416; and 5,269,775, among others.

Figure 2:
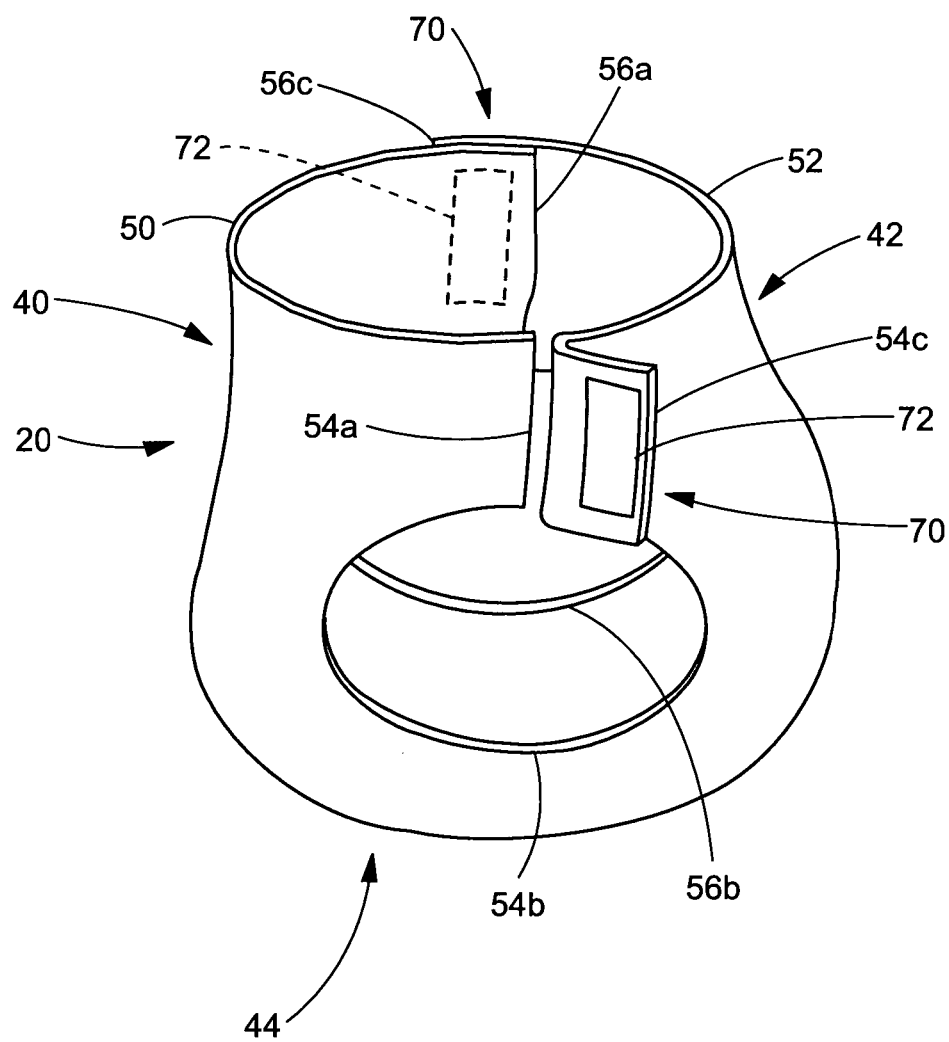
FIG. 2 is a perspective view of an exemplary absorbent article shown in its relaxed, contracted state, i.e., with the contraction induced by elastic members.

FIG. 2 illustrates the article illustrated in FIG. 1 configured to as it would be worn. The disposable absorbent article 20 may be sealed at the sides so as to be configured as illustrated in FIG. 2. However, the article 20 may instead include refastenable side seams 70 that can be used to fasten the waist regions 40, 42 together. According to one exemplary embodiment, the waist regions 40, 42 may be fastened at the sides to apply the article like a diaper. According to a further exemplary embodiment, illustrated in FIG. 2, the side seams 70 may include fasteners 72 that can be used to configure the article like a pair of pull-on training pants or disposable pants.

As illustrated, the fasteners 72 may be disposed on the interior of the disposable absorbent article 20 in the second waist region 42 adjacent to the portion 54c of the first side edge 54 and adjacent to the portion 56c of the second side edge 56. The portion 54c of the side edge 54 is shown in an open condition, such as prior to closing and fastening or after being reopened. The portion 56c of the opposing side edge 56 is shown fastened, i.e., forming a pants configuration. In FIG. 2, the second waist region 42 overlaps the first waist region 40 when they are fastened together.

The fasteners 72 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface.

Still other variations are also possible. For example, the fasteners 72 may be disposed on the interior of the article 20 in the first waist region 40 such that the first waist region 40 overlaps the second waist region 42 when they are fastened together. As another example, the fasteners 70 may be disposed on the exterior of the article 20 rather than on the interior. As a further example, the fasteners 70 may be used with a specific mating fastener surface particularly suited for cooperation with the fasteners 70 (e.g., a loop layer that works with a hook fastener, or a layer particularly treated to provide a suitable contacting surface for a specific adhesive). Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526, among others. Other fastener types may include "tab and slot" type mechanical refastenable fasteners. Buttons, snaps, zippers, and other types of fasteners, including refastenable fasteners are also possible.

According to the present disclosure, the exemplary article 20, such as is illustrated in FIGS. 1 and 2, may be combined with or assembled to include a sensation member 80. Several embodiments, some with one or more variations, are illustrated in FIGS. 3A, 3B, 5A, 5B, 6A, and 6B. Elements common to all embodiments are numbered similarly in all Figures, while those elements unique to each embodiment are numbered differently, with the sensation member according to a first embodiment being numbered as 80, a second embodiment as 180, and a third embodiment as 280. In addition, while certain exemplary absorbent articles illustrated include a single sensation member, the articles may include a plurality of sensation members.

Figure 3A:
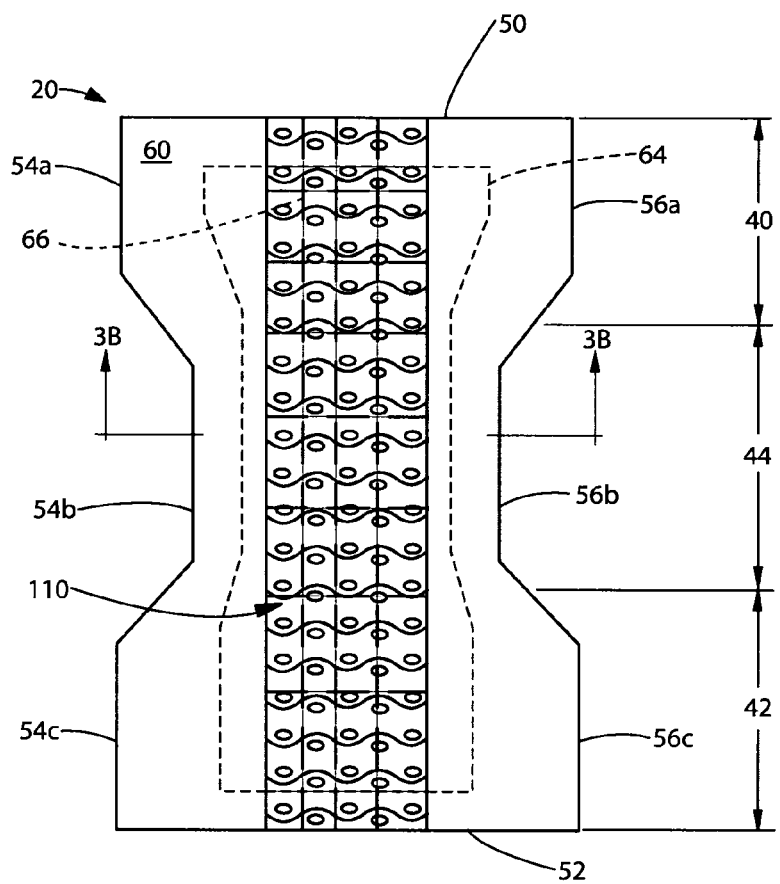
FIG. 3A is a plan view of an absorbent article having a sensation member according to an embodiment of the present disclosure.
Figure 3B:
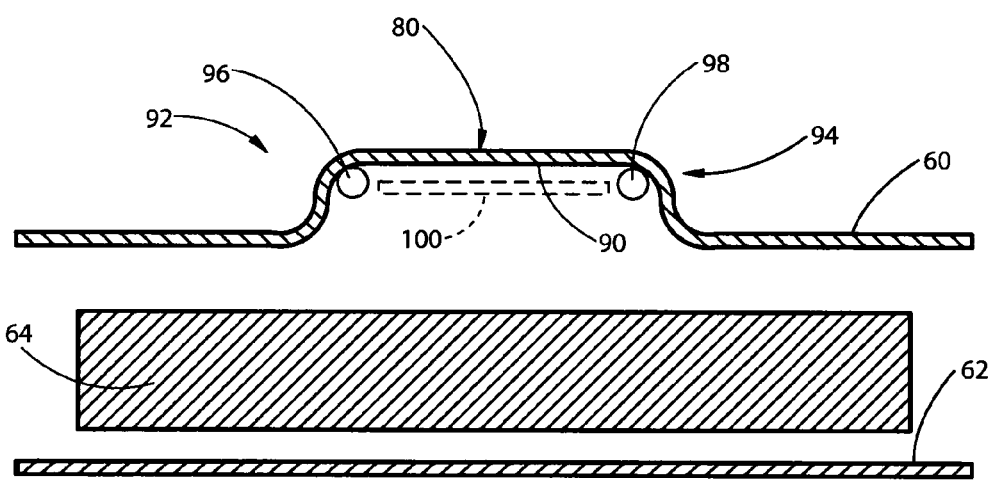

Referring now to FIGS. 3A and 3B, a fully or partially elasticized topsheet 60 can tend to draw a central region 90 upwards such that it is spaced from the absorbent core 64. The raised central region 90 is bound by a first side 92 and a second side 94 that both extend parallel to the longitudinal axis 30 of the article 20. A first elastic member 96 can be attached to the raised central region 90 of the topsheet 60 at the first side 92, while a second elastic member 98 can be attached to the raised central region 90 at the second side 94. The elastic members 96, 98 can extend along the entire length of the raised central region 90, or only a portion thereof.

As illustrated in FIGS. 3A and 3B, the sensation member 80 comprises at least a portion of the topsheet 60, for instance the raised central region 90 between the elastic members 96 and 98, that is at least partially impregnated, alternatively substantially impregnated, with a sensation agent. Accordingly, the sensation member 80 can be drawn upwards towards or against the skin of the wearer.

It should be appreciated that the sensation agent comprises one or more sensation materials that can impregnate all or a portion of the topsheet 60. For instance, referring to FIG. 3A, the topsheet 60 can be divided into one or more impregnation zones 66 bound as indicated by hidden lines. As illustrated, the impregnation zones 66 can be laterally aligned or longitudinally aligned. Furthermore, they can be co-planar with respect to the x-y plane, or could be non-coplanar (i.e., offset in the z-direction), for instance depending upon the mode of impregnation and the material that is impregnated or coated (as is described below, the present invention contemplates auxiliary sensation members). While each zone 66 includes a sensation material as illustrated, it should be appreciated that an individual zone or zones can be dedicated to one or more predetermined sensation materials, or not include a sensation material. Furthermore, the impregnation zones 66 can be shaped, sized, and positioned as desired to produce the desired sensation response to insults of urine.

Figure 4A:
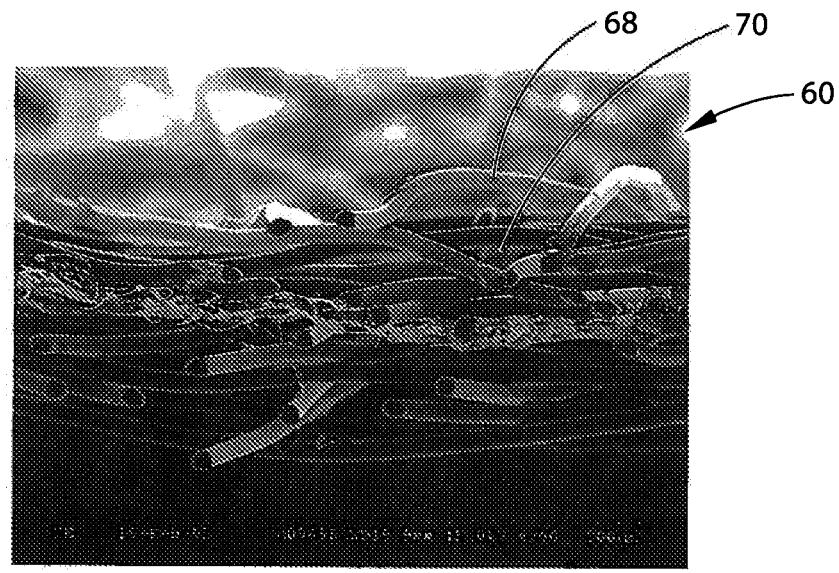
FIG. 4A is a surface electron microscopic image of a cross-section of an exemplary topsheet.
Figure 4B:
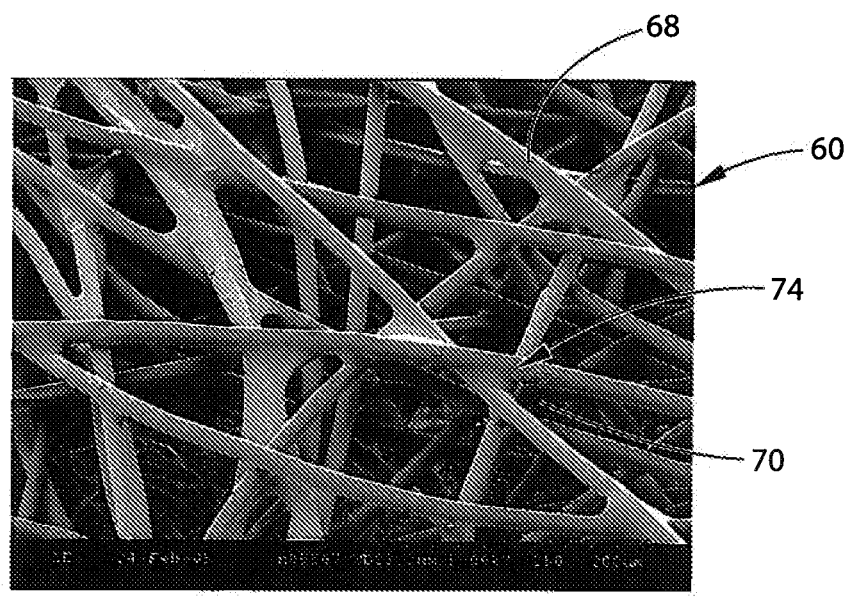
FIG. 4B is an image similar to that illustrated in FIG. 4a but with the fibers of the topsheet coated with a sensation material.
Figure 4C:
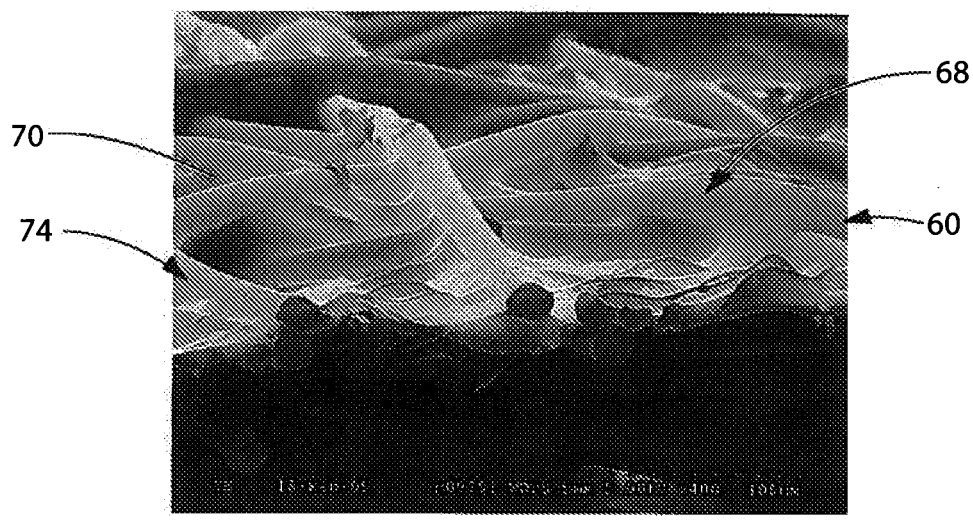
FIG. 4C is an image similar to that illustrated in FIG. 4b but with the fibers of the topsheet coated with a sensation material and with interstices between fibers filled with a sensation material.

It should be further appreciated that impregnation can occur in more than one mode. For instance, referring to FIG. 4A, a surface electron microscopic image of an exemplary topsheet 60 illustrates one or more layers of a plurality of fibers 68 that are overlap to form interstices 70 therebetween. In a first mode, as illustrated in FIG. 4B, a given zone of the topsheet 60 can be impregnated by at least partially coating individual interior fibers 68 (as opposed to merely the surface fibers 68) with a given sensation material 74, thus maintaining the interstices 70 between adjacent fibers. One method of achieving the first mode of impregnation is to coat the constituent topsheet 60 fibers 68 prior to forming them into a web, either by spraying, immersing, etc. In a second mode, a given zone of the topsheet 60 can be impregnated both by coating the individual fibers 68 and by filling the interstices 70 with the sensation material 74, as illustrated in FIG. 4C. This may be accomplished by slot coating or immersing at least a portion of the topsheet 60 web. In still another mode, the interstices 70 can be filled with a given sensation material 74 without substantially coating the individual fibers 68. This may be achieved by applying the coating initially in a fine particulate form and mechanically forcing the particles into the interstices 70 (e.g., via pressure, vibration, etc.), and, optionally, subsequently heating the web and particles slightly to at least partially melt the particles.

The coating can be applied in a molten or liquid form which is subsequently allowed to solidify or dry via evaporation, leaving a solid or semi-solid coating. The thickness of the coating, and the degree of penetration, can be controlled by the melting point and applications temperature of the composition, the concentration of the coating composition in the applied material, the temperature of the web or local environment, and subsequent heating and/or cooling of the coated web.

If the topsheet is non-fibrous, for instance an apertured film, impregnation can be accomplished by at least partially filling the apertures.

Figure 4D:
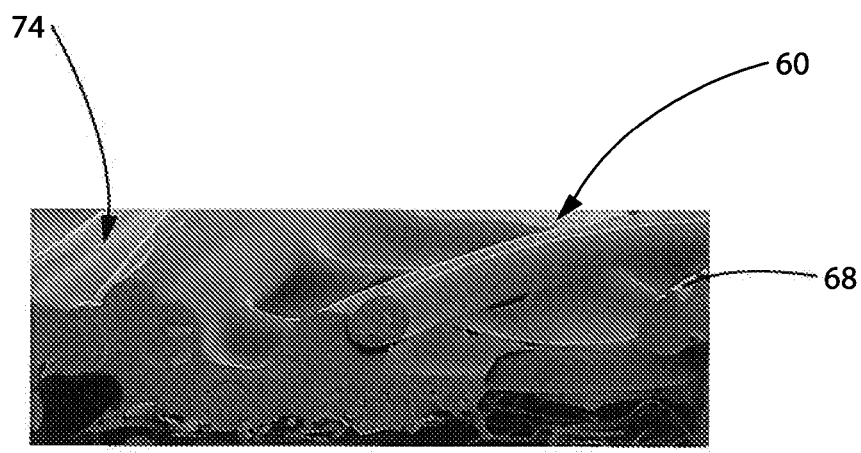
FIG. 4D is an image similar to that illustrated in FIG. 4c but with the topsheet substantially impregnated.

The topsheet 60 can be partially impregnated with the sensation material as illustrated in FIG. 4C meaning that in a given impregnation zone, only a portion of the total interstitial volume is occupied by the material and/or only a portion of the total surface area of the fibers in the region is coated with the material. Alternatively, as illustrated in FIG. 4D, the topsheet 60 can be substantially impregnated, meaning that in a given region of topsheet impregnation, substantially all of the total interstitial volume is substantially filled with the material and/or substantially all of the fibrous surface area is substantially completely coated with the material in the desired topsheet region.

It should thus be understood that, unless otherwise specified, the term "impregnated," "impregnation," or other variations of the word "impregnate" as used herein refer to any one of the modes of impregnation disclosed above, alone or in combination, unless otherwise specified. It should further be appreciated that the term "sensation material" as used herein includes a single sensation material present alone or in combination with other sensation materials. If more than one material is used in combination, it should be appreciated that the materials can be mixed, and the mixture can impregnate the topsheet 60, or that the materials can be impregnated at different zones 66 of the topsheet 60, or that the materials can be impregnated in the same zone of the topsheet 60 but at different locations throughout the thickness of the topsheet 60. Furthermore, the materials can be impregnated using different modes of impregnation.

In one embodiment, the sensation material is impregnated into the surface of topsheet 60 closer to the wearer's skin (i.e., body-facing surface), though the sensation material can be impregnated in any manner described above, and can be disposed anywhere between, and including, the body-facing surface and the opposing garment-facing surface of the topsheet 60 so long as the impregnated zone of the topsheet 60 provides a sensation to the skin of the wearer in response to an insult of urine.

The spacing of the first and second sides 92, 94 of the layer 90 and the degree of impregnation may be determined to allow enough liquid to travel to the core 64 so as to prevent flooding. Flooding may result in leakage of the article 20 during urination, which is undesirable in the article 20 when it is a diaper or training pant, for example. Consequently, it will be recognized that the dimensions of the layer 90 and the degree of impregnation may be determined to prevent flooding while at the same time wicking sufficient liquid to create a sensation of wetness or temperature change for the user.

During insults of urine, the raised region 90 allows urine to penetrate in the z-direction and also provides a medium for the flow of urine in the x-y plane via wicking. When the raised region 90 comprises the sensation member 80, or is provided in combination with an auxiliary sensation member as described in more detail below, the movement of the passage of the urine in the x-y plane can be enhanced, thereby expanding the wetted area of the sensation member, which preferably is held in contact with the wearer's skin. The wicking in the x-y plane causes the urine to spread out and effectively wet a large area before being absorbed into the absorbent assembly, thereby maximizing the signal experienced by the wearer.

In fact, the sensation member 80 may have a high initial wetness that dries out after, for example, approximately 10 minutes. That is, while the initial wetness may vary whether the raised region 90 is provided alone, or in combination with a sensation agent, the preferred response would be for the initial wetness to be sufficient to cause the wearer to recognize the condition, and the wetness over time to be limited so as not to create, for example, skin health issues because of too much wetness being present near the skin over a prolonged period of time.

In one aspect of the present invention, the sensation member 80 can comprise a temperature sensation agent formed from one or more materials that can at least partially impregnate or, alternatively, substantially impregnate the topsheet 60 at a desired impregnation region (for instance raised central region 90). In one embodiment, the temperature sensation material is impregnated into the surface of topsheet 60 closer to the wearer's skin (i.e., body-facing surface), though it can be appreciated that the temperature sensation material can be impregnated in any manner described above, and can be disposed anywhere between, and including, the body-facing surface and the opposing garment-facing surface of the topsheet 60 (or a layer disposed beneath the topsheet as described in more detail below) so long as the change in temperature is transferred to the skin of the wearer.

It will be recognized that the temperature sensation materials include those materials that produce a temperature change (i.e., involve an endothermic or an exothermic reaction), as well as sensates, which are defined as those materials that produce the sensation that a temperature change has occurred without necessarily undergoing an actual temperature change. For instance, while actual temperature changes may be slightly effected (i.e., changes in body heat, heat transfer from the urine, ambient environment, etc), the sensate produces a sensation of temperature change that is greater than any actual temperature change.

Exemplary temperature sensation materials include a cooling material. Further, the cooling material may be the AQUACOOL dye manufactured by United Polymer Technology of Akron, Ohio. The AQUACOOL dye is a water-soluble dye that changes temperatures when brought into contact with water. Another example of a cooling material includes a menthol or a menthol derivative, which chemicals are believed to provide the sensation of a temperature change, while not actually producing a temperature change. The COOLACT P and COOLACT 10 products manufactured by LIPO Chemicals of Paterson, N.J. are examples of menthol derivative products which may be suitable. Other examples of temperature change materials (e.g., endothermic salts) that may provide suitable temperature sensation agents may be found in U.S. Pat. No. 6,642,427. Such salts can be saturated in a liquid or gel, as is known to those having ordinary skill in the art, which can be impregnated into the topsheet 60. Alternatively, the salts may be applied to the topsheet in an aqueous solution, followed by a drying step in which the water carrier is evaporated, leaving the salt deposited on the topsheet fibers throughout at least a portion of the thickness of the web. In a still further alternative embodiment, the salt may be encapsulated between a wearer facing layer and a garment facing layer, at least one of which may comprise the topsheet, and wherein at least a portion of at least the wearer facing layer is liquid permeable.

If the temperature sensation agent effects an actual temperature change, the change should be of a sufficient magnitude to be noticed by the wearer. A temperature change of at least 5° C. might be desired to be noticeable. Cool receptors in the skin are most sensitive at about 25° C. (representing a temperature change of about 12° C. from body temperature). Cool signal activity is still high at 20° C., and the body typically senses "cool" down to about 15° C. Temperatures lower than 10 to 15° C. are perceived as "cold." It, therefore, may be desirable to provide a temperature change signal greater than about 5° C., preferably about 10-15° C., or a change of up to about 25° C. It may also be desired in some embodiments to have a cold signal (a large temperature change) for children who do not easily perceive more mild "cool" signals. Such a "heavy duty" or less easy to ignore cold signal could be provided by a cooling member which cools the skin to a temperature of less than about 15° C. Skin temperatures of less than 10° C., however, should be avoided since such temperatures are perceived as "noxious cold" and start to result in "burning pain." Such signals would not accomplish one of the design objectives of "harmless" described above.

Alternatively, or additionally, the sensation member 80 comprises a hydrophilic agent that increases the hydrophilicity of the topsheet 60 where impregnated with the hydrophilic material. A diverse range of hydrophilic materials can be used including lotions, creams and the like. Exemplary hydrophilic materials include surfactants, such as the NUWET silicone surfactant available from GE Silicones of Wilton, Conn.

The increased hydrophilicity of the topsheet 60 is useful for the purpose of alerting the wearer to an insult of urine, and allows the urine to be maintained for a period of time in the topsheet 60, thereby providing a sensation to the wearer. The hydrophilic material can be impregnated into the surface of topsheet 60 closer to the wearer's skin (i.e., body-facing surface), though it can be appreciated that the temperature sensation agent can be impregnated anywhere between, and including, the body-facing surface and the opposing garment-facing surface of the topsheet 60 in any manner described above, such that the wearer experiences a wetness sensation in response to an insult of urine.

Alternatively, or additionally, the sensation member 80 comprises a tactile agent that produces a sensation at the wearer's skin in response to an insult of urine. Tactile agents can comprise an effervescent material that produces a mild concussive (i.e., "popping," "crackling," "bubbling," or "fizzing") sensation at the wearer's skin. Examples of such effervescent materials are disclosed in U.S. Pat. No. 6,929,819.

In one aspect, the effervescent material is a urine soluble solid material produced whereby a pressurized gas is trapped within cells located in the solid material. When the solid material is contacted with urine, it begins to dissolve and the pressurized gas is released from the cells creating a noticeable sensation on the wearer's skin, thereby alerting the wearer to the urination. The effervescent material may comprise a sugar compound (such as a mono-saccharide, di-saccharide, or poly-saccharide), salts, alkali halides, and alkaline earth metal halides infused with a gas that is substantially non-reactive with human skin such as carbon dioxide, air, nitrogen, argon, helium, etc. Specific examples of suitable saccharides include glucose, fructose, sucrose, lactose, maltose, dextrin, cyclodextrin, and the like, alone or in combination. The procedure for producing a gas containing solid material is set forth in U.S. Pat. No. 4,289,794.

In another aspect, the effervescent material comprises a mixture of compounds, such as an acid and a base, that when wetted with urine, react and produce a gaseous product and the wearer is alerted to having urinated through a "bubbling" or "fizzing" sensation on the skin. The effervescent material could be in the form of a mixture of acid powders and base powders, liquid acids and liquid bases, or combinations thereof. The solid acids and bases can be provided neat or in microencapsulated form.

One having ordinary skill in the art will appreciate that the effervescent agent can be at least partially impregnated or substantially impregnated into the topsheet 60, particularly at the raised region 90 to provide the wetness sensation member 80.

Alternatively or additionally, the tactile agent comprises one or more dimensional change materials that rapidly undergo a change in at least one dimension when exposed to an aqueous solution. The dimensional change can be an expansion to at least 2 times a dry dimension or a contraction to less than about one-half (½) of the dry dimension. In particular embodiments, the dimensional change is either an expansion to at least about 5 times the dry dimension or a contraction to less than about one-fifth (⅕) of the dry dimension. Examples of such dimensional change materials are described in U.S. Pat. No. 5,702,376.

For instance, the dimensional change material can comprise a compressed cellulose sponge, expandable foams, or the like. Particularly desirable expandable foams include those having open, large cell, reticulated structures. Examples of such expandable foams are available from O-Cell-O, General Mills, Inc., Tonawanda, N.Y., USA, and Industrial Commercial Supply Co., Akron, Ohio, USA. If the dimensional change material increases in height when exposed to liquid, it may be desirable to provide a plurality of sponge materials to be contained in the topsheet 60, thus filling interstitial voids 70 and at least partially impregnating the topsheet. Accordingly, upon exposure to liquid, the sponge particles expand and apply a pressure to the body-facing surface of the topsheet without deforming the topsheet structurally. Alternatively, if the sponge material is designed to contract in response to exposure to a liquid, the sponge material can be introduced into the topsheet 60 at a location and in sufficient quantity that pressure is initially applied to the body-facing surface of the topsheet. Accordingly, upon exposure to liquid, the sponge particles will contract in height and the pressure against the body-facing surface will subside. Alternatively, a layer of sponge material can be provided as an auxiliary sensation member 200a (described below with reference to FIG. 5b).

Alternatively or additionally still, the dimensional change material can comprise porous absorbent polymeric macrostructures (formed from AGM macrostructures made of fine particles) as described in U.S. Pat. No. 5,124,188, the disclosure of which is incorporated by reference. Other rapid-swelling AGMs can also provide the dimensional change material, as could compressed structures held under compression by urine soluble materials. Examples of absorbent articles containing mechanical actuating structures can be found in U.S. Pat. Nos. 3,881,491; 3,921,232; 5,330,459; and 6,186,991.

In accordance with another aspect of the present invention, the sensation member 80 comprises a hydrophobic agent that decreases the hydrophilicity of the topsheet 60 where impregnated with a hydrophobic material. The hydrophobic material can, for instance, be impregnated in various zones 66 of the topsheet 60 such that liquid is directed into more hydrophilic zones 66 that are aligned with the wearer's body for the purposes of increasing wetness sensation in response to an insult of urine.

Examples of hydrophobic materials include lotions, creams and the like, skin care compositions such as those described in U.S. Pat. Nos. 5,607,760; 5,609,587; 5,635,191; 5,643,588; 5,968,025; 6,118,041; 6,120,488; 6,120,783; 6,153,209; 6,156,024; and 6,166,285. Further examples of hydrophobic materials include acrylic polymers (e.g., acrylamide, ethyl alcohol, n-butyl alcohol, methyl-methacrylate, acrylonitrile, or combinations thereof) emulsions manufactured and sold, for example, under the ROHATOL tradename by Lanxess Corp. of Pittsburg, Pa., the RH-MW 1845K tradename by Rohm & Haas of Philadelphia, Pa., or the FA1, FA2, or FA3 tradenames by PolymerLatex International GmbH of Marl, Germany.

The signal generated by the sensation member 80 desirably contacts the wearer's skin to elicit a sensation. In some embodiments, the absorbent article 20 and sensation member 80 are designed to enable at least intermittent, and preferably virtually continuous, contact between the wearer facing surface of the sensation member and the wearer's skin in all body positions and during all activities in which the wearer may engage. It may be desirable for the area of contact on the wearer's body to be an area having a relatively higher concentration of nerve endings. In the region of the body commonly covered by disposable absorbent articles such as pant-like diapers or training pants, the genital, perineal, perianal, inner thigh, and lower abdomen have a relatively higher nerve concentration are the preferred contact areas.

One method of promoting contact between the sensation member and the wearer is to provide a raised sensation member as described herein. In these embodiments, the skin contact is affected by providing a sensation member at least locally detached from underlying layers in at least the desired region of contact and elastically foreshortening the sensation member, or a structure to which the sensation member is affixed, causing the sensation member 80 to be lifted in the z-direction toward the body. Additionally, in certain embodiments, the elastic lifting members cause the sensation member 80 to contact the body with sufficient force and resiliency to allow the sensation member to continue to contact the body during wearer motion, or to quickly re-establish contact in the event that contact is temporarily broken.

Other methods of promoting skin contact may also be employed in place of, or in addition to the method described hereinabove. For example, at least a portion of the skin contacting surface of the article 20 may comprise a contact promoting substance that adheres gently to the wearer's skin and resists casual disengagement. Exemplary contact promoting substances may include skin care compositions such as lotion as described in U.S. Pat. Nos. 5,607,760; 5,609,587; 5,635,191; 5,643,588; 5,968,025; 6,118,041; 6,120,488; 6,120,783; 6,153,209; 6,156,024; and 6,166,285, sticky lotions as described in International Patent Application WO 2004/087092, and adhesives such as body adhesives. In certain embodiments a water-activatable adhesive may be desirable as it would only promote contact once the wearer urinates. Water activatable adhesives for use in disposable absorbent articles are disclosed in U.S. Pat. No. 6,623,465. The skin contact promoting substance may be disposed on at least a portion of the sensation member 80 or in a region of the topsheet 60 or other supporting structure in proximity to the sensation member 80.

Skin contact may also be promoted via resilient 3-dimensional structures comprising foams or core materials. These structures serve to hold the sensation member in contact with the wearer even during wearer motion due to their 3-dimensional resilient nature. In some embodiments, these structures may be relatively thin and unobtrusive when in a dry state and may be triggered to grow in the z-direction by contact with urine. For example, the structure may comprise a compressed foam encapsulated in a water or pH sensitive material wherein the foam is allowed to expand upon contact with urine or the structure may comprise a composition capable of evolving gas held within a semi-permeable membrane such that it inflates upon contact with urine. Further examples of structures that increase in thickness upon contact with urine include those described in U.S. Pat. Nos. 3,881,491; 3,921,232; 5,330,459; 6,186,991; 5,797,892; 5,428,076; and 5,124,188.

The disposable absorbent article 20 may have indicia, such as visible highlighting 110 as illustrated in FIG. 3a as an exemplary pattern of wavy lines and circles, in the interior of the article associated with the topsheet 60 to indicate the presence of the sensation member 80 and thereby facilitate an opportunity for the urinary toilet training of the wearer of the article. Such visible highlighting is described in U.S. Published Application No. 2005/0096612. Although a topsheet 60 including a sensation member that lacks the visible highlighting is fully functional in terms of providing a noticeable wetness and/or temperature signal to the wearer, the caregiver might overlook or forget the possibility of capitalizing on each opportunity for urinary toilet training if the body-facing portion of the absorbent article presents a generally uniform appearance, such as in absorbent articles that present a generally uniform white appearance on their body-facing surfaces.

Furthermore, once the caregiver decides to mention urinary toilet training to the wearer, the visible highlighting can serve to draw the wearer's interest or can be pointed out by the caregiver and incorporated into an explanation of the upcoming opportunity. Thus, the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the sensation member.

Even a simple solid coloring form of visible highlighting can serve to facilitate an opportunity for urinary toilet training, especially when used with wearers possessing some recognition of colors or colored forms. In addition, visible highlighting in the form of a color or colors may facilitate the teaching of recognition of colors and differences between colors and the associated learning may enhance the urinary toilet training process in turn.

Because the impregnated topsheet 60 is located in what may be generally termed the laterally central region of the absorbent article 20, visibly highlighting the topsheet 60 may provide additional benefits related to the learning achieved by the wearer. For example, a visibly highlighted topsheet may provide a line of reference for the visual separation of the two leg openings, including their differentiation into right and left leg openings for the respective feet to be inserted into the corresponding leg openings. Similarly, a longitudinally oriented visible highlighting may serve as a visual reference for the front to back direction, both for orienting the article prior to applying it, if done by the caregiver, or prior to donning it, if done by the wearer. This longitudinally oriented visual reference may also aid in the teaching of such skills as wiping one's self clean after using the toilet by using a longitudinal motion. The concept of something being central or "in the middle" may be taught and learned by visual reference to the visible highlighting and this concept may then be applied to related subjects, such as the anatomical location of the source of urine and the corresponding proper position in which to sit on the toilet. Thus, in the above and similar ways, the wearer can be made more aware of his or her own body, which may tend to enhance and facilitate the urinary toilet training experience.

In addition, the visible highlighting can serve to enhance the self-esteem of the wearer through a reminder that he or she is mature enough to be engaged in urinary toilet training. This effect can be compounded when the wearer succeeds in recognizing the need to go to the toilet and then sees the dry condition of the visibly highlighted topsheet 60 inside the article after pulling it down.

The visible highlighting may be provided by means of printing onto a surface of the topsheet 60. For example, solid coloring or a graphic may be printed onto a surface of the body-facing surface of the topsheet 60 or the garment-facing surface of the topsheet 60. As another example, an adhesive or a gel may be printed onto a surface of either of the topsheet. Such an adhesive or gel may be colored differently from the surrounding area. Alternatively, the adhesive or gel may be uncolored or may have the same color as the surrounding area, but may still provide visible highlighting by forming a distinctive raised area or pattern and/or by surrounding a distinctive recessed area or pattern.

The visible highlighting may also be provided by forming one or more layers of the topsheet 60 of a colored material, for example, a fibrous layer containing colored fibers, a monolithic layer containing a dispersed or imbedded colorant, a layer of an unbleached material that is colored in its virgin state, and so on.

In some embodiments, the visible highlighting may be provided by impressing or embossing the topsheet 60. The impressed, embossed, or bonded portions of the topsheet 60 may include tactile members that provide a tactile sensation in addition to visibly highlighting the presence and location of the sensation member 80. For instance, a raised area or a recessed area or the combination of raised and recessed areas adjacent to each other may be felt by the hand and, in some embodiments, may be felt by the wearer while wearing the article. Similarly, the raised area or pattern formed by a printed adhesive or gel, as mentioned above, may provide such a tactile sensation. Just as with the visible highlighting alone, the combination of visible highlighting and this tactile sensation can serve to draw the wearer's interest or can be pointed out by the caregiver and incorporated into an explanation of the upcoming opportunity for urinary toilet training.

In addition, the visible highlighting may be provided by incorporating distinctive fibers or filaments in the topsheet 60 or by distinctively orienting fibers or filaments in the topsheet 60. For example, a fiber or a filament of a distinctive color may be incorporated into the coating to visibly highlight its presence and its location in the article. Similarly, a distinctively thicker fiber or filament may be embedded in one of the two layers and thereby form a distinctive raised area or pattern.

If the portions of the structure of the absorbent article 20 surrounding the topsheet 60 are of one color, the visible highlighting can be provided by the use of another color, by the use of contrast, by the use of a different pattern in the same or a similar color, or by any other method that visibly differentiates the topsheet 60 containing the sensation member 80 from the surrounding structural elements.

In some embodiments, the visible highlighting may include more than one color, more than one difference in contrast, more than one pattern, more than one graphic, more than one area of solid coloring, and so on, such that all portions of this description referring to the singular of a form of visible highlighting are meant to include the plural, and vice versa.

The visible highlighting may include open or closed geometric figures, a two dimensional representation of a three dimensional object, a representation of a commonly named or nameable shape or object, a representation of a recognizable object used in play, and/or a representation of a character that may be known to the wearer, such as a teddy bear, a character appearing on a television show for children, a character appearing in a game or a storybook for children, etc. In embodiments in which the visible highlighting includes a variety of figures, objects, and/or characters, the various elements of the visible highlighting may be interactively inter-related, related by subject matter, and/or related by a common story line. Conversely, the various elements may be interactively unrelated, unrelated by subject matter, and/or not related by a common story line.

When solid coloring is used, it may partially or completely fill the area bounded by a graphic outline, appear as shading inside or outside such a graphic outline, itself form a "filled-in" graphic, or simply uninterruptedly occupy an area, e.g., occupy the entire width of the topsheet 60 over all or a portion of the corresponding length.

In some embodiments, the visible highlighting may become more or less visible, or change color, when the region (s) of the topsheet 60 providing the sensation member 80 is wetted. Any of these effects may be created by the use of inks or dyes or other agents that undergo chemical reactions or are dispersed or concentrated when wetted by urine. In general, any of the wetness indicating compositions commonly used in externally visible wetness indicators, such as so-called "appearing" or "disappearing" wetness indicators that may become more or less visible when wetted and in wetness indicators that may change color when wetted, may be used for these versions of visible highlighting.

It is important to note that rather than being structurally disposed in such a way as to provide a wetness indication that is visible from the outside of the absorbent article, according to at least one embodiment, any wetness indicating compositions used for the visible highlighting of the topsheet 60 should be visible from the body-facing surface of the absorbent article. This different disposition enables the caregiver to apply different techniques to the task of urinary toilet training when using an absorbent article of the present disclosure, as compared to using an absorbent article having only a wetness indicator visible from the outside of the article. For example, while the change in an exterior wetness indicator is visible for all to see, any change in the visible highlighting of remains "private" until either the caregiver or the wearer peers into the absorbent article or it is removed. Therefore, whether or not any wetting of the absorbent article has occurred can, itself, become the focus of a playful activity resembling a game, with the "secret" being revealed only when the caregiver and the wearer agree to conclude the game. If the wearer notices a sensation of wetness or merely desires to check the condition of the "private" indication, he or she can simply look inside the absorbent article. If the appearance of the visible highlighting has changed, the wearer can then choose to bring this to the attention of the caregiver in the context of asking to go to the bathroom. In addition, because the visible highlighting serves as a "private" indication, the wearer might be able to detect a change in its appearance before the appearance of any externally visible wetness indicator changes and thereby be the first person to mention the subject of going to the toilet. Furthermore, the provision of both visual and tactile sensations to the wearer may serve to reinforce the tactile sensation of wetness and thereby enhance the training effect of the sensation member 80. An absorbent article in which the wetting is indicated by both a sensation and a visible change in the appearance of the visible highlighting may thus facilitate faster learning on the part of the wearer.

Although the appearance of the visible highlighting remains "private" until either the caregiver or the wearer peers into the absorbent article or it is removed, the visible highlighting may be associatively correlated in visible form with marking that is located elsewhere in or on the absorbent article and is visible from the outside of the absorbent article. This externally visible marking may be permanent or may change in appearance while the absorbent article is being worn. For example, the externally visible marking may be an externally visible wetness indicator. By giving the visible a visible form that is similar to the visible form of an externally visible marking, an opportunity for urinary toilet training may be enhanced. For instance, the caregiver can point out the similarity between the externally visible marking and the "private" visible highlighting of the topsheet 60 and ask the wearer to remember the hidden visible highlighting every time he or she notices the externally visible marking.

For example, the article 20 may comprise an internal graphic 110, a first external graphic, and a second external graphic. The internal graphic may be permanent, while the external graphics may be "appearing" or "disappearing." The first external graphics may include a character image resembling a boy and a text graphic including words forming a message, such as "Remember to go to the potty!" While the graphics may include text, the primary form of communication may be symbols, icons, or other markings other than words, so that a pre-literate child may comprehend and follow the instructions or other information indicated by the graphics, although it is not necessary for the images to be understood at this level. The second external graphics may include an image that may be associatively correlated to the permanent graphic, such as a dog or stars.

Variations regarding the internal/external graphics are possible. For example, a permanent external image may be combined with the first and second external graphics, or only one external graphic may be included. Furthermore, character images other than a boy may be provided, such as a girl, an animal (which may be anthropomorphic), a cartoon character, and the like. Still further, additional or alternative text may be provided. Additionally exemplary graphics, graphics characteristics and/or arrangements (e.g., timings, themes, scenes, storylines, etc.), the materials that are suitable for forming the graphics, and the arrangement and/or joining of these materials to the article 20 are described in co-pending and commonly assigned U.S. patent application Ser. No. 11/098,362, filed in the name of Roe et al. on Apr. 4, 2005.

Even in embodiments in which the appearance of the visible highlighting is not affected by its being wetted, the associative correlation of the respective visible forms of an externally visible marking and the visible highlighting may serve to facilitate an opportunity for urinary toilet training. For example, if both the externally visible marking and the visible highlighting have the visible form of similar graphics, the externally visible marking can serve to draw the wearer's interest or can be pointed out by the caregiver and incorporated into an explanation of the ongoing opportunity for urinary toilet training.

Such associative correlation of the respective visible forms of an externally visible marking and the visible highlighting can be achieved without the respective visible forms being similar, so long as the respective visible forms are mutually related in a recognizable way. For example, the visible forms may be related in subject matter and/or may be related by a common story line and/or be interactively interrelated. Even an associative correlation of a simple solid coloring form of an externally visible marking with a similar solid coloring form of visible highlighting can serve to facilitate an opportunity for urinary toilet training, especially when used with wearers possessing some recognition of colors or colored forms.

Alternatively, the visible highlighting may be associatively uncorrelated with any externally visible marking. The lack of associative correlation may be complete or may be specific, e.g., the respective visible forms of the visible highlighting and the externally visible marking may be unrelated in subject matter, not related by a common story line, and/or interactively unrelated, while still being associatively correlated in another way.

The visible form of the visible highlighting of the topsheet 60 need not be associatively correlated with the concept of urinary toilet training. However, in some embodiments, the visible form of the visible highlighting may be associatively correlated with the concept of urinary toilet training by, for example, providing a visual reference to the liquid-related nature of urinary toilet training, such as wetness, dryness, protection from wetness, the flow of a liquid, water, et cetera, and thus may serve to facilitate an opportunity for urinary toilet training.

The visible highlighting may emphasize dryness by depicting the sun, fair weather clouds, a sunny day, etc., while wetness may be referenced by a depiction of a water puddle, a cloud with falling rain, etc. A visual reference to protection from wetness may be provided by a depiction of an umbrella, a raincoat, a rain hat, galoshes, a submarine, or some other object that may be associated by the wearer with the concept of staying dry in a wet environment.

In any of these visible forms of visible highlighting that are associatively correlated with the concept of urinary toilet training, a human form and/or a recognizable character may be depicted in the visible highlighting. For example, a child may be shown in conjunction with inanimate objects, a child may be shown sitting on a potty chair, and/or a character from a children's storybook or a children's television program may be shown in similar poses, etc.

With further reference to FIG. 3B, the absorbent article 20 can further include an auxiliary sensation member 100 disposed below the topsheet 60, and in the illustrated embodiment is a coating applied to the garment-facing surface of the raised central region 90 of the topsheet 60. The auxiliary sensation member 100 can be a coating applied to the garment-facing surface of the topsheet 60, such that the coating is disposed in a face-to-face arrangement with the topsheet 60. The coating can comprise any of the sensation materials described above, and in one embodiment comprises materials that form a hydrophobic agent that can be applied in discrete zones 66 of the raised region 90 of the topsheet 60 that prevent liquid from passing through to the core 64. The zones 66 can be determined so as to be aligned with the skin of the wearer's body such that wetness of the topsheet 60 will be maintained and sensed by the user. Alternatively, the auxiliary sensation member can extend substantially along the entirety of the garment-facing surface of the topsheet 60 or, alternatively, of the raised portion of the topsheet 90.

The spacing of the first and second sides 92, 94 of the layer 90 and the width of the coating, if present, may be determined to allow enough liquid flow to the core 64 so as to prevent flooding. Consequently, it will be recognized that the dimensions of the layer 90 and the auxiliary sensation member 100 may be determined to prevent flooding while at the same time wicking sufficient liquid to create a sensation of wetness for the user.

The coating can further comprise a temperature sensation agent of the type described above. As a result, when the coating experiences an insult of urine, a temperature decrease can occur at the coating that is sensed by the wearer's skin. Alternatively, the coating can include a sensate that produced a sensation of temperature decrease (or increase) without necessarily undergoing an actual temperature change. In other words, the sensed temperature change is greater than any actual temperature change.

It should be appreciated that the coating can include the hydrophobic agent and the temperature sensation agent alone or as a mixture. Alternatively still, the hydrophobic agent and temperature sensation agent can be coated on the garment-facing surface of the topsheet 60 at discrete locations as desired.

Alternatively, auxiliary sensation member 100 can comprise a discrete layer of material constructed as described above with reference to the topsheet 60. In this embodiment, the auxiliary sensation member 100 can be oriented proximal to the garment-facing surface of the topsheet 60, and can extend across the entire length and width of the topsheet 60 or a portion thereof, for instance along the entire length and width of the raised region 90 or a portion of the raised region 90. The auxiliary sensation member 100 can be impregnated by any of the wetness sensation materials described above with respect to the coating, for instance the temperature sensation material and the hydrophobic material alone or in combination.

In one aspect of the present invention, the zone or zones 66 of the topsheet 60 that are impregnated with one or more sensation materials has an amount of moisture contacting the skin that should be of a sufficient quantity to be noticed by the wearer. For example, a surface Moisture Density (as measured by the Moisture Density Test) of greater than about 2 mg/cm$^2$ at 60 seconds or greater than about 4 mg/cm$^2$ at 60 seconds or greater than about 5 gm/cm$^2$ at 60 seconds may be desired. The wetness desirably does not persist for an undue period of time. For example, it may be desired that the surface Moisture Density at 10 minutes is less than about 80% or less than about 75% or less than about 70% of the surface Moisture Density measured at 60 seconds.

Figure 5A:
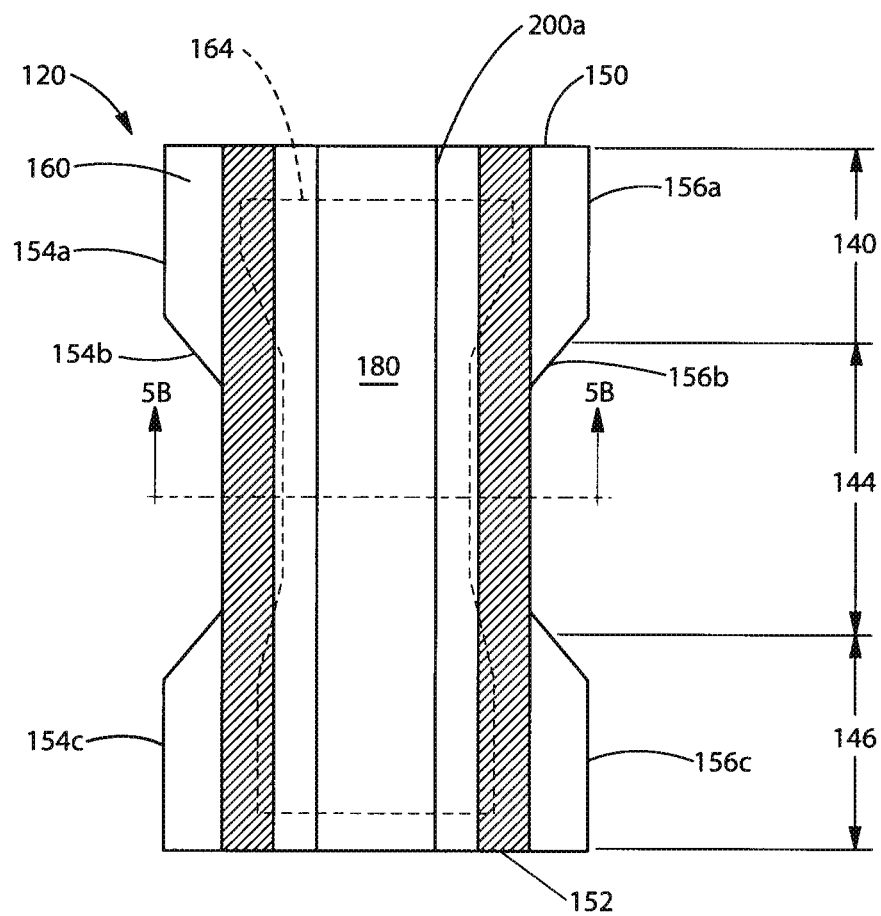
FIG. 5A is a plan view of an absorbent article having a sensation member according to another embodiment of the present disclosure.
Figure 5B:
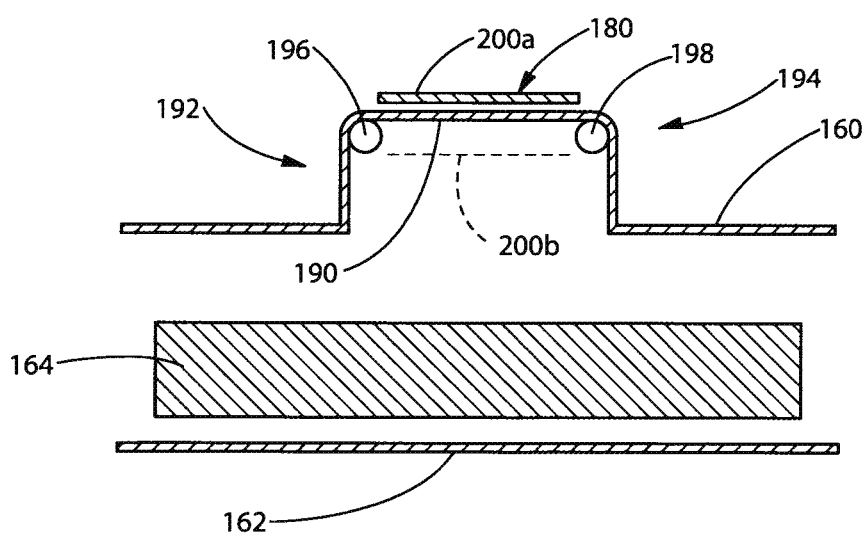

Turning next to FIGS. 5A and 5B, a second embodiment of an absorbent article 120 is illustrated whereby like reference numerals corresponding to elements illustrated in FIGS. 3A and 3B have been incremented by 100. Similar to the absorbent article 20 illustrated in FIGS. 3a and 3b, the topsheet 160 includes a raised central region 190 that is upwardly spaced from the absorbent core 164. The raised central region 190 is bound by a first side 192 and a second side 194 that both extend parallel to the longitudinal axis of the article 120. A first elastic member 196 can be attached to the central raised region 190 of the topsheet 160 at the first side 192, while a second elastic member 198 can be attached to the layer 190 at the second side 194. The elastic members 196, 198 can extend along the entire length of the layer 190, or only a portion thereof.

The absorbent article 20 illustrated in FIGS. 5A and 5B differs from that illustrated in FIGS. 3A and 3B in that an upper auxiliary sensation member 200a comprises a layer of material disposed proximal the body-facing surface of the topsheet 160, for instance at the central raised region 190 as illustrated. The sensation layer 200a is thus disposed in a face-to-face relationship with the body-facing surface of the topsheet 160. The sensation layer 200a can be formed from the same material from which the topsheet 160 is formed, and can be attached to the upper surface of the topsheet 160 in any desired manner. Accordingly, the upper auxiliary sensation member 200a is drawn into close contact with the skin of the wearer. It should be appreciated that the sensation layer 200a can extend the full length and width of the topsheet 160 or a portion thereof, for instance the full length and width of the raised region 190 or only a portion of the raised region 190.

The upper auxiliary sensation member 200a can be impregnated with any one or all of the sensation materials in the manner described above. Alternatively, or in addition, the upper layer 200a can be coated on its body-facing surface and/or its garment-facing surface with any one of the sensation materials alone or in combination. For instance, one or more sensation materials can be coated on top of one another. Alternatively, or additionally, certain sensation materials can be disposed adjacent one another. Additionally, the upper layer 200a can include a visible graphic 110 or indicia of the type described above, thus providing one or more of the above-described advantages.

It should also be appreciated that the topsheet 160, when provided in combination with the upper auxiliary member 200a, can be impregnated with any of the sensation materials as described above with reference to FIGS. 3A and 3B to provide wetness sensation member 180. Furthermore, the absorbent article 20 can include a lower sensation layer 200b that can be constructed as a discrete layer or a coating as described above with reference to auxiliary sensation member 100 of FIGS. 3A and 3B.

In one aspect of the present invention, the zone or zones 66 of the topsheet 160 or upper sensation layer 200a, if applicable, that are impregnated with one or more sensation materials has a surface Moisture Density (as measured by the Moisture Density Test) of greater than about 2 mg/cm$^2$ at 60 seconds or greater than about 4 mg/cm$^2$ at 60 seconds or greater than about 5 gm/cm$^2$ at 60 seconds may be desired. The wetness desirably does not persist for an undue period of time. For example, it may be desired that the surface Moisture Density at 10 minutes is less than about 80% or less than about 75% or less than about 70% of the surface Moisture Density measured at 60 seconds.

Figure 6A:
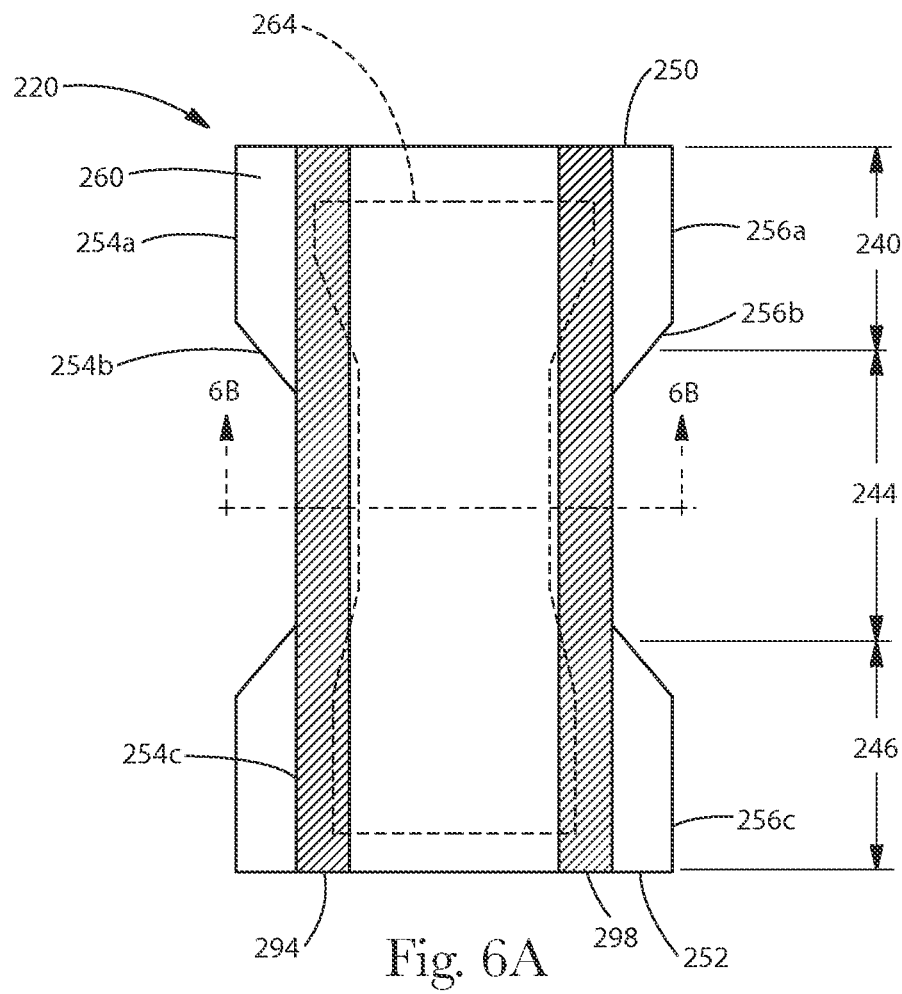
FIG. 6A is a plan view of an absorbent article having a sensation member according to a further embodiment of the present disclosure.
Figure 6B:
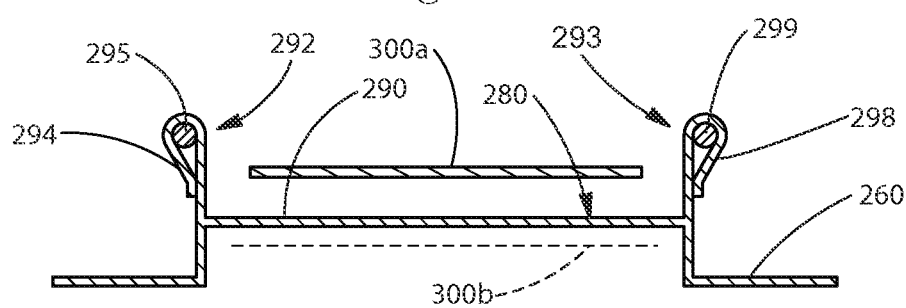
Figure 6B:
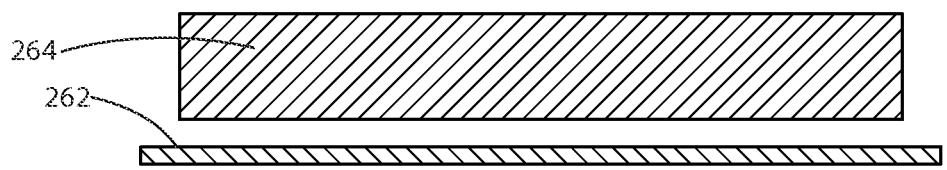

Referring now to FIGS. 6A and 6B, a third embodiment of the absorbent article 220 is illustrated with reference numerals corresponding to like elements of FIGS. 5A and 5B incremented by 100. The absorbent article 220 includes first and second barrier leg cuffs 294 and 298, respectively attached to the topsheet 260. The barrier leg cuffs 294 and 298 extend longitudinally substantially along the length of the absorbent article 220, or could extend along a portion of the article. The cuffs 294 and 298 are laterally spaced such that they are connected to the outer longitudinally extending edges 292 and 293 of the central raised region 290 of the topsheet 260. Moreover, each barrier leg cuff 294 and 298 includes an elastic member 295, 299. In this fashion, it is not necessary to attach separate elastic members to the topsheet 290, but rather the elastic members 295, 299 of the barrier leg cuffs 294, 298 can urge the sensation member topsheet into contact with the skin of the wearer.

In fact, it is believed that the attachment of the sensation member 280 to the barrier leg cuffs 294, 298 may permit greater control over the spacing of the raised region 290 relative to the core 264 (i.e., distance between raised region 290 and core 264) than had heretofore been possible.

Similar to the embodiment discussed above with respect to FIGS. 3A and 3B, the topsheet 260 can be impregnated with any of the sensation materials, either alone or in combination. Furthermore, as described above with respect to FIGS. 5A and 5B, the absorbent article no can include an upper auxiliary sensation member 300a and a lower auxiliary sensation member 300b. For instance, it may be desirable to provide the hydrophobic agent at one or more zones proximal the barrier leg cuffs 294 and 298 by impregnation of the topsheet 260 at locations proximal the barrier leg cuffs 294 and 298 for the purposes of providing a barrier against the leakage of urine. Alternatively, the hydrophobic agent can be disposed at the upper auxiliary sensation member 300a, which can be a coating of the topsheet 260, or can be a discrete layer of suitable material attached to the topsheet 260. The auxiliary sensation member 300a can then either be impregnated with one or more wetness sensation materials or coated with one or more wetness sensation materials in one or more of the zones 66 described above with reference to FIG. 3A.

Alternatively, as described above, it may be desirable for upper auxiliary sensation member 200a to comprise a tactile agent, for instance including the effervescent material or the dimensional change member.

In one aspect of the present invention, the zone or zones 66 of the topsheet 60 or upper auxiliary sensation member 200a, if applicable, that are impregnated with one or more sensation materials has a surface Moisture Density (as measured by the Moisture Density Test) of greater than about 2 mg/cm at 60 seconds or greater than about 4 mg/cm at 60 seconds or greater than about 5 gm/cm at 60 seconds may be desired. The wetness desirably does not persist for an undue period of time. For example, it may be desired that the surface Moisture Density at 10 minutes is less than about 80% or less than about 75% or less than about 70% of the surface Moisture Density measured at 60 seconds.

Furthermore, indicia 110 can be included on a surface of the topsheet 290 or, if applicable, the upper auxiliary sensation member 200a.

In addition to the features described above, the disposable absorbent article 20 may also include a variety of features known in the art, such as slit openings, outer leg cuffs, front and rear ear panels, waist cap features, elastics, and the like to provide desired fit, containment, and aesthetic characteristics. Such additional features are well known in the art and are described in U.S. Pat. Nos. 3,860,003; 5,151,092; and 6,482, 191 among others. Additionally, a transfer layer, which may also be referred to as an acquisition or distribution layer, may be disposed between the topsheet 60 and the core 64. Moreover, the elements discussed above may be modified from their illustrated forms.

Figure 7A:
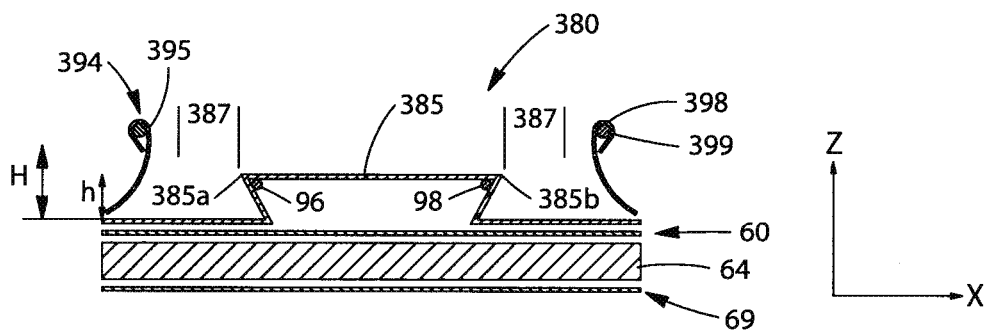
FIGS. 7A-7C are cross-sectional views of another embodiment of an absorbent article.
Figure 7B:
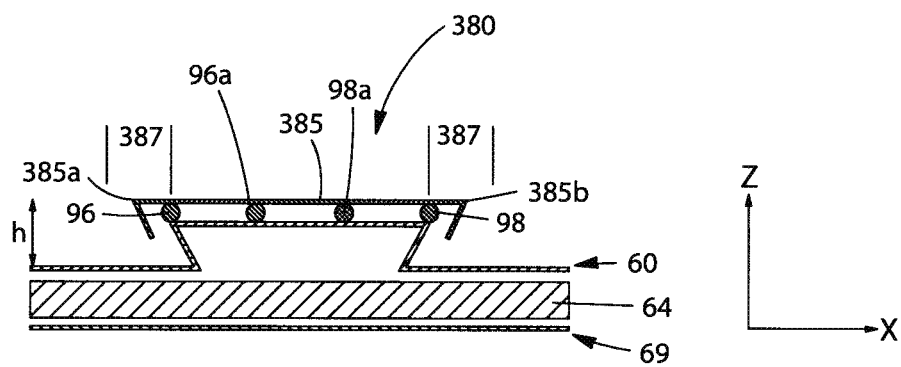
Figure 7C:
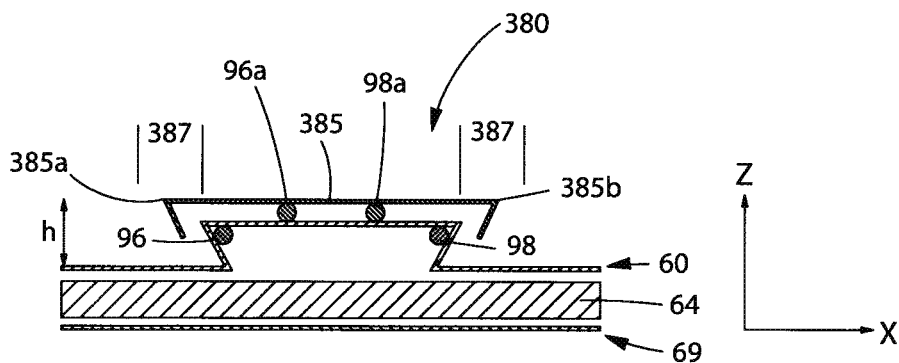

In additional embodiments shown in FIGS. 7A-7C, the sensation member 380 or any layer including the sensation member can be disposed in two parallel Z-folds 387 formed along the longitudinal length of the absorbent article. The Z-folded sensation member 380 or any layer including the sensation member may be attached to the underlying layers along the longitudinal edges of the topsheet 60 allowing the portion between the Z-folds of the topsheet 60 to float freely. Elastic elements 96, 98 may be disposed along the central region of the sensation member 380 in order to deflect the central region outward away from the absorbent core 64. Elastic elements 96, 98 may be disposed between layers of the topsheet 60, between layers of the sensation member 380, between the topsheet 60 and sensation member 380, or any other configuration that connects the elastic elements 96, 98 to the topsheet 60 and/or sensation member 380. The central region 385 may have a first side edge 385a and a second side edge 385b such that at least one of said side edges 385a, 385b has a projected height h measured the z direction between the side edge and the base of the sensation member that connects the sensation member to the absorbent article.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member.

The Z-folded sensation member 380 allows the central region 385 to be suspended away from the core 64 and the topsheet 60. The combination of the Z-folded sensation member 380 and the elastic elements 96, 98 maintains the sensation members in proximity to the wearer's skin in the event that the diaper sags or fits loosely around the wearer.

Alternatively, additional elastic elements 96a, 98a may be disposed along the central region of the Z-folded sensation member. Elastic elements 96a, 98a, may be disposed between layers of topsheet 60, between layers of the sensation member 380, between the topsheet 60 and sensation member 380, or any other configuration that connects the elastic elements 96a, 98a to the topsheet 60 and/or sensation member 380. Elastic elements 96a, 98a provide additional support to prevent sagging and promote contact with the wearer's skin.

The absorbent article may also include a first barrier leg cuff 394 and a second barrier leg cuff 398, which may include elastic members 395, 399 respectively. First and second barrier leg cuffs are disposed on the absorbent article such that the Z-folded sensation member 380 is located between the barrier leg cuffs 395, 399. At least one of the first barrier leg cuff 394 and a second barrier leg cuff 398 has a projected height H measured the z direction between an upper edge of the barrier leg cuff and the base of the barrier leg cuff that connects the barrier leg cuff to the absorbent article.

The projected height h and H may be measured according the following method.

A disposable absorbent article including a sensation member is attached to the inner surface of a curved plate (i.e. the concave surface relative to the hypothetical center of the circle having the same curvature as the plate) having a radius of curvature of about 250 mm. The disposable absorbent article is attached to the plate such that its garment facing surface (i.e. outer cover) is in contact with the plate. In this configuration, the elastic member(s) that are disposed longitudinally on the disposable absorbent article are in an elongated configuration and are applying a force that is pulling any layer attached to the elastic member away from the core. A ruler having one end contacting the base of the sensation member and the other end pointing toward the center of the hypothetical circle formed by the curved plate, may be used to measure the distance between the base of the sensation and the side edge of the sensation member. The side edge of the sensation member is gently extended to its maximum height (i.e. without applying a force that would cause the sensation member to be torn or destroyed) and then record the measurement. The projected height measurement can be repeated at various points along the sensation member in order to determine its maximum projected height. The ruler may be moved such that one end is in contact with the base of an outer leg cuff and its other end is pointing towards the center of the hypothetical circle passing through the curved plate. The projected height H may be determined by measuring distance between the base of the outer leg cuff and the upper edge of the outer leg cuff. The upper edge of the outer leg cuff is gently extended to its maximum height (i.e. without applying a force that would cause the outer leg cuff to be torn or destroyed) and then record the measurement. The projected height measurement can be repeated at various points along the outer leg cuff in order to determine its maximum projected height.

In one embodiment, the projected height h of at least one of the first side edge 385a and a second side edge 385b is between 90% and 300%, preferably between 100% and 250%, more preferably between 100% and 200% of the projected height H of at least one of the first barrier leg cuff 394 and a second barrier leg cuff 398.

In one embodiment, the projected height h of at least one of the first side edge 385a and a second side edge 385b is between 15 mm and 50 mm, preferably between 20 mm and 45 mm, more preferably between 25 mm and 40 mm.

Figure 8:
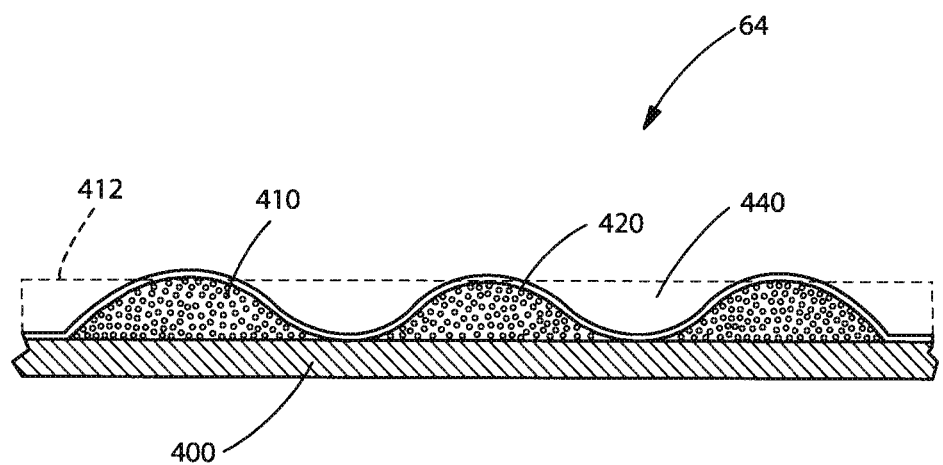
FIG. 8 is a cross-sectional view of an embodiment of the absorbent core.

One preferred embodiment of the present invention includes, but is not limited to, articles described in U.S. Patent Application No. 2004/0162536 and U.S. Patent Application No. 2004/0167486. The aforementioned applications are directed to absorbent articles having an absorbent core which imparts increased wearing comfort to the article and makes it thin and dry. As shown in FIG. 8, the absorbent articles of the present invention may comprise an absorbent core 64 comprising a substrate layer 400, absorbent polymer material 410 and a fibrous layer of adhesive 420. The substrate layer 400 is preferably provided from a non-woven material, preferred non-wovens include those provided from synthetic fibers, such as PE, PET and PP. As the polymers used for non-woven production are inherently hydrophobic, they are preferably coated with hydrophilic coatings.

In accordance with the present invention, the absorbent material is immobilized when wet such that the absorbent core achieves a wet immobilization of more than 50%, preferably of more than 60%, 70%, 80% or 90%.

The substrate layer 400 comprises a first surface and a second surface. At least portions of the first surface of the substrate layer 400 are in direct contact with a layer of absorbent polymer material 410. This layer of absorbent polymer material 410 is preferably a discontinuous layer, and comprises a first surface and a second surface. As used herein, a discontinuous layer is a layer comprising openings. Typically, these openings have a diameter or largest span of less than 10 mm, preferably less than 5 mm, 3 mm, 2 mm and a span of more than 0.5 mm, 1 mm or 1.5 mm. At least portions of the second surface of the absorbent polymer material layer 410 are in contact with at least portions of the first surface of the substrate layer material 400. The first surface of the absorbent polymer material 410 defines a certain height 412 of the layer of absorbent polymer above the first surface of the layer of substrate material 400. When the absorbent polymer material layer 410 is provided as a discontinuous layer, portions of the first surface of the substrate layer 400 are not covered by absorbent polymer material 410. The absorbent core 64 further comprises a thermoplastic composition 420. This thermoplastic composition 420 serves to at least partially immobilize the absorbent polymer material 410.

In one preferred embodiment of the present invention the thermoplastic composition 420 can be disposed essentially uniformly within the polymeric absorbent material 410.

However, in an even more preferred embodiment of the present invention the thermoplastic material 420 is provided as a fibrous layer which is partially in contact with the absorbent polymer material 410 and partially in contact with the substrate layer 400. In this preferred structure the absorbent polymer material layer 410 is provided as a discontinuous layer, a layer of fibrous thermoplastic material 420 is laid down onto the layer of absorbent polymeric material 410, such that the thermoplastic layer 420 is in direct contact with the first surface of the layer of absorbent polymer material 410, but also in direct contact with the first surface of the substrate layer 400, where the substrate layer is not covered by the absorbent polymeric material 410. This imparts an essentially three-dimensional structure to the fibrous layer of thermoplastic material 420 which in itself is essentially a two-dimensional structure of relatively small thickness (in z-direction), as compared to the extension in x- and y-direction. In other words, the fibrous thermoplastic material layer 420 undulates between the first surface of the absorbent polymer material 410 and the first surface of the substrate layer 400.

Thereby, the thermoplastic material 420 provides cavities to hold the absorbent polymer material 410, and thereby immobilizes this material. In a further aspect, the thermoplastic material 420 bonds to the substrate 400 and thus affixes the absorbent polymer material 410 to the substrate 400. Highly preferred thermoplastic materials will also penetrate into both the absorbent polymer material 410 and the substrate layer 400, thus providing for further immobilization and affixation.

Of course, while the thermoplastic materials disclosed herein provide a much improved wet immobilization (i.e., immobilization of absorbent material when the article is wet or at least partially loaded), these thermoplastic materials also provide a very good immobilization of absorbent material when the article is dry.

In accordance with the present invention, the absorbent polymer material 410 may also be mixed with absorbent fibrous material, such as airfelt material, which can provide a matrix for further immobilization of the super-absorbent polymer material. However, preferably a relatively low amount of fibrous cellulose material is used, preferably less than 40 weight %, 20 weight %, or 10 weight % of cellulose fibrous material as compared to the weight of absorbent polymer material 410. Substantially airfelt free cores are preferred. As used herein, the term "absorbent fibrous material" is not meant to refer to any thermoplastic material 420 even if such thermoplastic material is fiberized and partially absorbent.

The absorbent core of the present invention may further comprise a cover layer. This cover layer may be provided of the same material as the substrate layer 400, or may be provided from a different material. Preferred materials for the cover layer are the non-woven materials. In this embodiment, portions of the cover layer bond to portions of the substrate layer 400 via the thermoplastic material 420. Thereby, the substrate layer 400 together with the cover layer provides cavities to immobilize the absorbent polymer material 410.

The areas of direct contact between the thermoplastic material 420 and the substrate material 400 are referred to as areas of junction 440. The shape, number, and disposition of the areas of junction 440 will influence the immobilization of the absorbent polymer material 410. The areas of junction can be of squared, rectangular, or circular shape. Preferred areas of junction are of circular shape. Preferably, they have a diameter of more than 0.5 mm, or 1 mm, or 1.5 mm and of less than 10 mm, or 5 mm, or 3 mm, or 2 mm. If the areas of junction 440 are not of circular shape, they preferably are of a size as to fit inside a circle of any of the preferred diameters given above.

The areas of junction 440 can be disposed in a regular or irregular pattern. For example, the areas of junction 440 may be disposed along lines. These lines may be aligned with the longitudinal axis of the absorbent core, or alternatively, they may have a certain angle in respect to the longitudinal edges of the core. It has been found, that a disposition along lines parallel with the longitudinal edges of the absorbent core 64 create channels in the longitudinal direction which lead to a lesser wet immobilization. Preferably, therefore the areas of junction 440 are arranged along lines which form an angle of 20 degree, 30 degree, 40 degree, or 45 degree with the longitudinal edges of the absorbent core 64. Another preferred pattern for the areas of junction 440 is a pattern comprising polygons, for example pentagons and hexagons or a combination of pentagons and hexagons. Also preferred are irregular patterns of areas of junction 440, which also have been found to give a good wet immobilization.

Two fundamentally different patterns of areas of junctions 440 can be chosen in accordance with the present invention. In one embodiment, the areas of junctions are discrete. They are positioned within the areas of absorbent material, like islands in a sea. The areas of absorbent materials are then referred to as connected areas. In an alternative embodiment, the areas of junctions can be connected. Then, the absorbent material can be deposited in a discrete pattern, or in other words the absorbent material represents islands in a sea of thermoplastic material 420. Hence, a discontinuous layer of absorbent polymer material 410 may comprise connected areas of absorbent polymer material 410 or may comprise discrete areas of absorbent polymer material 410.

In a further aspect of the present invention, it has been found that absorbent cores providing for a good wet immobilization can be formed by combining two layers. In this embodiment, the absorbent core material comprises two substrate layers 400, two layers of absorbent polymer material 410 and two layers of fibrous thermoplastic materials 420. When two discontinuous layers of an absorbent polymer material 410 are used, they would be typically arranged in such a way that the absorbent polymer material of the one layer faces the areas of junction 440 of the other layer. In an alternative preferred embodiment, however, the areas of junction 440 are offset and do not face each other.

According to the present invention, the thermoplastic layer 420 can comprise any thermoplastic composition, preferred are adhesive thermoplastic compositions, also referred to as hot melt adhesives. A variety of thermoplastic compositions are suitable to immobilize absorbent material. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behaviour are herein also understood as thermoplastic materials 420.

In embodiments of the present disclosure, a disposable wearable absorbent article can include a stretchable outer cover. For example, the outer cover can be a uniaxially stretchable outer cover, configured to stretch in one direction. Also as an example, the outer cover can be a biaxially stretchable outer cover, configured to stretch in two directions. In various embodiments, the outer cover can be configured as described in U.S. non-provisional patent application entitled "Biaxially Stretchable Outer Cover for an Absorbent Article," filed on Nov. 15, 2006 with Express Mail No. EV916939625 and further identified by attorney docket number 10643, which is hereby incorporated by reference.

In embodiments of the present disclosure, a disposable wearable absorbent can include an outer cover configured in various ways, including configurations of part or all of the outer cover as stretchable, non-stretchable, with an elastic nonwoven, with an elastic film and extensible nonwoven, with an extensible film and an elastic nonwoven, pre-stretched with elastic strands allowed to contract, mechanically activated, with zero strain laminate, and/or combinations of these and any other outer cover configurations. In various embodiments of the present disclosure, a disposable wearable absorbent article can include a printed outer cover with various basis weights, chemistries, and/or mechanical activations, as will be understood by one of ordinary skill in the art.

Relative Surface Moisture Density Test Method:

This test simulates the introduction of urine into a training pant diaper. No pressure is applied while loading to simulate the baby urinating in a standing position.

Equipment:

| | |
|---|---|
| Template | Flat Base unit on which to mount the test product |
| Filter Paper | Ahlstrom Filtration Paper Code 632, 127 × 127 mm |
| Balance | accuracy +/− 0.01 g |
| Saline | 0.9% Saline heated to 37° C. +/− 1° C. |
| Graduated Cylinder | Convenient Source |
| Timer | Convenient Source, time measurements taken to nearest second |
| Weight | Plastic Dimensions/Weight 127 × 127 mm, 297 grams |
| Metal Cyliner | Metal Cylinder, Inside Diameter = 60 mm, Outside Diameter = 70 mm, Height = 40 mm, Weight = 327 grams |

Test Procedure
 1. Test fluid is 0.9% saline heated to 37° C.±1° C.
 2. If the product is provided in a closed, pant-like form, open side seams of all products. If product contains defined side seams product should be opened at those locations. Otherwise, cut side panels with scissors at midpoint of side panels.
3. Mount the test product with clamps onto a flat template in a flat stretched out condition to ensure no wrinkles in the topsheet or liners. The pant elastics should stay intact.
4. Weigh one piece of filter paper.
5. Measure as follows to define the loading point
   (boy) 10.2 cm below front edge of the core, or
   (girl) 12.7 cm below front edge of the core.
   (unisex or generic) use boy loading point measurement
6. Measure 75 mls of 0.9 saline (heated to 37° C.±1° C.) into the graduated cylinder.
7. Center the cylinder over the loading point and pour the saline from the graduated cylinder at the loading point. Loading should be done over approximately 5 seconds or at approximately 15 mL/second.
8. Once fluid is poured, start timer. Pouring the saline is considered to be the "urination event" for purposes of comparison of time with time parameters in the claims.
9. After 60 seconds have elapsed, place filter paper on the topsheet and then the plastic weight to ensure complete contact between the filter paper and the topsheet. The weight should be lowered slowly and applied gently to the filter paper.
10. After 10 seconds from weight application, lift the weight and filter paper off of the topsheet and weigh the filter paper.
11. Calculate wet weight minus dry filter paper weight in mg. This value is divided by 161.29 cm$^2$ to determine the wetness density in mg/cm$^2$.

It should be noted further, that this testing protocol can be adjusted easily according to specific product types, such as different diaper sizes, for use with other types of absorbent articles, such as adult incontinence devices, or catamenial devices. The type and amount of loading fluid, the amount and size of the absorbent material, or the applied pressure may also be varied to suit individual product needs. Such modifications will be obvious to one skilled in the art.

All documents cited in the Detailed Description are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An absorbent article comprising:
   a backsheet having a longitudinal axis;
   a topsheet attached to the backsheet and having a body-facing surface and first and second sides;
   an absorbent core disposed between the backsheet and the topsheet;
   first and second spaced barrier leg cuffs attached to the topsheet parallel to the longitudinal axis, each barrier leg cuff comprising at least one elastic member;
   wherein a portion of a central region of said body-facing surface of said topsheet disposed between the first and second barrier leg cuffs is lifted, relative to the absorbent core, in a z-direction toward a wearer's body by the elastic members of the barrier leg cuffs to define a raised portion having a first outer longitudinally extending edge and a second outer longitudinally extending edge, wherein the raised portion of said topsheet is spaced from all absorbent cores in the absorbent article;
   wherein the first spaced barrier leg cuff is attached to the first outer longitudinally extending edge of the raised portion, and the second spaced barrier leg cuff is attached to the second outer longitudinally extending edge of the raised portion;
   wherein the elastic members of the first and second spaced barrier leg cuffs are located laterally outboard of the raised portion of the topsheet; and
   a sensation member comprising said topsheet at least partially impregnated with a sensation agent.

2. The absorbent article of claim 1 wherein said sensation agent is selected from the group consisting of a hydrophilic agent, a hydrophobic agent, a temperature change agent, a tactile agent, and combinations thereof.

3. The absorbent article of claim 2 wherein said hydrophobic agent is disposed proximal the barrier leg cuffs.

4. The absorbent article of claim 2 further comprising an auxiliary sensation member disposed beneath said topsheet, said auxiliary sensation member comprising the hydrophobic agent.

5. The absorbent article of claim 4 wherein said hydrophobic agent is at least partially impregnated in said auxiliary sensation member.

6. The absorbent article of claim 4 wherein said hydrophobic agent comprises a coating of said auxiliary sensation member.

7. The absorbent article of claim 2 wherein said temperature change agents include endothermic salts.

8. The absorbent article of claim 1, wherein said topsheet is impregnated with at least two sensation agents.

9. The absorbent article of claim 8 wherein said sensation agents are disposed at discrete zones of the topsheet, said zones being laterally or longitudinally spaced from each other.

10. The absorbent article of claim 8 wherein at least a portion of said sensation agents is in vertical alignment.

11. The absorbent article of claim 1 wherein said sensation member has a first Moisture Density of at least about 2 mg/cm$^2$ at 60 seconds after said urination event and a second Moisture Density at 10 minutes after said urination event of less than about 80% of said first Moisture Density.

12. The absorbent article of claim 1 wherein said topsheet is comprised of fibers some of which are at least partially coated with said sensation agent.

13. The absorbent article of claim 1 wherein said topsheet is comprised of a fibrous matrix having interstitial void spaces in which said sensation agent is at least partially contained.

14. The absorbent article of claim 1 wherein the article is a diaper, pant or refastenable pant.

15. The absorbent article of claim 1 wherein said sensation agent is substantially impregnated in the topsheet.

16. The absorbent article of claim 1 further comprising indicia indicating the presence of said sensation agent, said indicia being visible or tactile.

* * * * *